United States Patent
Hammerberg et al.

(10) Patent No.: US 12,060,437 B2
(45) Date of Patent: Aug. 13, 2024

(54) METHODS AND COMPOSITIONS FOR ANTIBODY TO HIGH AFFINITY RECEPTOR FOR IgE

(71) Applicant: North Carolina State University, Raleigh, NC (US)

(72) Inventors: Bruce Hammerberg, Raleigh, NC (US); Sitka Eguiluz-Hernandez, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 858 days.

(21) Appl. No.: 16/982,765

(22) PCT Filed: Mar. 22, 2019

(86) PCT No.: PCT/US2019/023515
§ 371 (c)(1),
(2) Date: Sep. 21, 2020

(87) PCT Pub. No.: WO2019/183437
PCT Pub. Date: Sep. 26, 2019

(65) Prior Publication Data
US 2023/0192894 A1 Jun. 22, 2023

Related U.S. Application Data

(60) Provisional application No. 62/647,385, filed on Mar. 23, 2018.

(51) Int. Cl.
| | | |
|---|---|---|
| *C07K 16/42* | (2006.01) | |
| *C07K 14/735* | (2006.01) | |
| *C07K 16/28* | (2006.01) | |
| *G01N 33/50* | (2006.01) | |
| *A61K 39/00* | (2006.01) | |

(52) U.S. Cl.
CPC .... *C07K 16/4291* (2013.01); *C07K 14/70535* (2013.01); *C07K 16/283* (2013.01); *G01N 33/5091* (2013.01); *A61K 2039/505* (2013.01); *C07K 2317/34* (2013.01); *C07K 2317/622* (2013.01); *G01N 2800/24* (2013.01)

(58) Field of Classification Search
None
See application file for complete search history.

(56) References Cited

U.S. PATENT DOCUMENTS

| | | |
|---|---|---|
| 4,399,216 A | 8/1983 | Axel et al. |
| 4,740,461 A | 4/1988 | Kaufman |
| 4,816,567 A | 3/1989 | Cabilly et al. |
| 4,912,040 A | 3/1990 | Kaufman et al. |
| 4,946,778 A | 8/1990 | Ladner et al. |
| 4,959,455 A | 9/1990 | Clark et al. |
| 5,091,313 A | 2/1992 | Chang |
| 5,254,671 A | 10/1993 | Chang |
| 5,258,498 A | 11/1993 | Huston et al. |
| 5,260,203 A | 11/1993 | Ladner et al. |
| 5,260,416 A | 11/1993 | Chang |
| 5,342,924 A | 8/1994 | Chang et al. |
| 5,428,133 A | 6/1995 | Chang |
| 5,514,776 A | 5/1996 | Chang |
| 5,530,101 A | 6/1996 | Queen et al. |
| 5,585,089 A | 12/1996 | Queen et al. |
| 5,599,677 A | 2/1997 | Dowell et al. |
| 5,614,611 A | 3/1997 | Chang |
| 5,672,480 A | 9/1997 | Dowell et al. |
| 5,693,761 A | 12/1997 | Queen et al. |
| 5,693,762 A | 12/1997 | Queen et al. |
| 5,760,185 A | 6/1998 | Kimachi et al. |
| 5,958,708 A | 9/1999 | Hardman et al. |
| 5,959,177 A | 9/1999 | Hein et al. |
| 5,994,511 A | 11/1999 | Lowman et al. |
| 6,040,498 A | 3/2000 | Stomp et al. |
| 6,043,345 A | 3/2000 | Saxon et al. |
| 6,180,370 B1 * | 1/2001 | Queen ............... C07K 16/2803 |
| | | 435/69.6 |
| 6,267,958 B1 | 7/2001 | Andya et al. |
| 6,423,512 B1 | 7/2002 | Digan et al. |
| 6,504,013 B1 | 1/2003 | Lawton et al. |
| 6,841,659 B2 | 1/2005 | Turpen et al. |
| 6,852,319 B2 | 2/2005 | Hein et al. |
| 6,881,557 B2 | 4/2005 | Foote |
| 7,148,023 B2 | 12/2006 | Hammerberg |
| 7,244,580 B2 | 7/2007 | Gershwin et al. |
| 7,247,711 B2 | 7/2007 | Benson et al. |
| 7,261,890 B2 | 8/2007 | Krah et al. |
| 7,384,633 B2 | 6/2008 | Sugimura et al. |

(Continued)

FOREIGN PATENT DOCUMENTS

| | | |
|---|---|---|
| CN | 101633698 A | 1/2010 |
| JP | H0792167 | 4/1995 |

(Continued)

OTHER PUBLICATIONS

Kipriyanov, Sergey M., and Fabrice Le Gall. "Generation and production of engineered antibodies." Molecular biotechnology 26.1 (2004): 39-60. (Year: 2004).*
Janeway, Charles A. "Immunobiology: The Immune System in Health and Disease." 2001 (Year: 2001).*
International Search Report and the Written Opinion of the International Searching Authority corresponding to International Patent Application No. PCT/US2019/23515 (11 pages) (mailed Jul. 25, 2019).
Justice et al. "Using the mouse to model human disease: increasing validity and reproducibility" Disease Models & Mechanisms, 9:101-103 (2016).
Saha et al. "DNA Vaccines: A Mini Review" Recent Patents on DNA & Gene Sequences, 5:92-96 (2011).
Ames et al. "Omalizumab" Nature Reviews Drug Discovery, 3(3):199-200 (2004).

(Continued)

*Primary Examiner* — Michael Szperka
*Assistant Examiner* — Lia E Taylor
(74) *Attorney, Agent, or Firm* — Myers Bigel, P.A.

(57) ABSTRACT

The present invention is directed to an antibody that specifically binds an IgE receptor and methods of its use.

14 Claims, 3 Drawing Sheets

Specification includes a Sequence Listing.

(56) References Cited

U.S. PATENT DOCUMENTS

| | | | |
|---|---|---|---|
| 7,470,773 | B2 | 12/2008 | Hammerberg |
| 7,736,648 | B2 | 6/2010 | Kauvar et al. |
| 7,781,647 | B2 | 8/2010 | Bakker et al. |
| 7,816,334 | B2 | 10/2010 | Rice et al. |
| 7,867,494 | B2 | 1/2011 | Liu et al. |
| 7,897,153 | B1 | 3/2011 | Braren et al. |
| 7,910,702 | B2 | 3/2011 | Kav et al. |
| 7,943,144 | B2 | 5/2011 | Brown et al. |
| 8,017,146 | B2 | 9/2011 | Stefano et al. |
| 8,025,898 | B2 | 9/2011 | Houze et al. |
| 8,036,738 | B2 | 10/2011 | Sirkar et al. |
| 8,041,421 | B2 | 10/2011 | Birchall et al. |
| 8,043,250 | B2 | 10/2011 | Xu |
| 8,043,830 | B2 | 10/2011 | Barat et al. |
| 8,067,005 | B1 | 11/2011 | Chapman et al. |
| 8,071,097 | B2 | 12/2011 | Wu et al. |
| 8,071,333 | B2 | 12/2011 | Giles-Komar et al. |
| 8,076,456 | B2 | 12/2011 | Mattson et al. |
| 8,080,249 | B2 | 12/2011 | Risk |
| 8,097,704 | B2 | 1/2012 | Kim et al. |
| 8,101,175 | B1 | 1/2012 | Croft et al. |
| 8,101,184 | B2 | 1/2012 | Li et al. |
| 8,101,423 | B2 | 1/2012 | Cunningham et al. |
| 8,101,727 | B2 | 1/2012 | Stover et al. |
| 8,105,598 | B2 | 1/2012 | Dimitrov et al. |
| 8,252,907 | B2 | 8/2012 | Krah et al. |
| 8,460,664 | B2 | 6/2013 | Chang et al. |
| 9,546,219 | B2 | 1/2017 | Hammerberg |
| 11,352,443 | B2 | 6/2022 | Hammerberg et al. |
| 2002/0107359 | A1 | 8/2002 | Hogarth et al. |
| 2003/0190318 | A1 | 10/2003 | Torigoe et al. |
| 2003/0229021 | A1 | 12/2003 | Krah et al. |
| 2007/0161066 | A1 | 7/2007 | Hammerberg |
| 2009/0117124 | A1 | 5/2009 | Liu et al. |
| 2009/0252732 | A1 | 10/2009 | Siadak et al. |
| 2010/0040606 | A1 | 2/2010 | Lantto et al. |
| 2010/0040619 | A1 | 2/2010 | Li et al. |
| 2010/0061988 | A1 | 3/2010 | Hansen |
| 2010/0129380 | A1 | 5/2010 | McKenzie et al. |
| 2013/0171137 | A1* | 7/2013 | Mitre .................. C07K 16/283 424/153.1 |
| 2014/0286958 | A1 | 9/2014 | Bammert et al. |
| 2015/0010547 | A1 | 1/2015 | Hammerberg |
| 2015/0344581 | A1 | 12/2015 | Bilsborough |
| 2016/0280799 | A1 | 9/2016 | Bouche et al. |
| 2018/0230236 | A1 | 8/2018 | Hammerberg et al. |
| 2021/0009678 | A1 | 1/2021 | Hammerberg et al. |

FOREIGN PATENT DOCUMENTS

| | | |
|---|---|---|
| WO | 8801649 A1 | 3/1988 |
| WO | 9804718 A1 | 2/1998 |
| WO | 2006048781 A2 | 5/2006 |
| WO | 2008106980 A2 | 9/2008 |
| WO | 2013119419 A1 | 8/2013 |
| WO | 2014201525 A1 | 12/2014 |
| WO | 2015003406 A1 | 1/2015 |
| WO | 2016133197 A1 | 8/2016 |

OTHER PUBLICATIONS

Bachmann et al. "Vaccination against IL-31 for the treatment of atopic dermatitis in dogs" Journal of Allergy and Clinical Immunology, 142:279-281 (2018).

Bird et al. "Single-Chain Antigen-Binding Proteins" Science, 242(4877):423-426 (1988).

Blubaugh et al. "The anti-inflammatory effects of topical tofacitinib on immediate and late-phase cutaneous allergic reactions in dogs: a placebo-controlled pilot study" Vet. Dermatol., 2 pages (2018) (Abstract only).

Boyce, Thomas G. "Gastroenteritis" Merck Manuals Professional Edition, 7 pages, downloaded Mar. 22, 2021.

Brunner et al. "Early-onset pediatric atopic dermatitis is characterized by TH2/TH17/TH22-centered inflammation and lipid alterations" Journal of Allergy and Clinical Immunology, 141(6):2094-2106 (2018).

Corren et al. "Effects of omalizumab, a humanized monoclonal anti-IgE antibody, on nasal reactivity to allergen and local IgE synthesis" Annals of Allergy, Asthma & Immunology, 93(3):243-248 (2004).

Cretien et al. "A Monoclonal Anti-IgE Antibody Against An Epitope (Amino Acids 367-376) in the CH3 Domain Inhibits IgE Binding to the Low Affinity IgE Receptor (CD23)" The Journal of Immunology, 141(9):3128-3134 (1988).

De Graaf et al. "Expression of scFvs and scFv fusion proteins in eukaryotic cells" Methods in Molecular Biology, 178:379-387 (2002).

Dehlink et al. "A Soluble Form of the High Affinity IgE Receptor, Fc-epsilon-RI, Circulates in Human Serum" PLoS One, 6(4):e19098 (Apr. 2011).

Dog Purified Immunoglobulin, BethyLaboratories, Medline, 2 pages (2004).

Edwards et al. "The Remarkable Flexibility of the Human Antibody Repertoire; Isolation of Over One Thousand Different Antibodies to a Single Protein, BLyS" Journal of Molecular Biology, 334:103-118 (2003).

Eggel et al. "Inhibition of Ongoing Allergic Reactions Using a Novel anti-IgE DARPin-Fc Fusion Protein" Allergy, 66(7):961-968 (2011).

European Medicines Agency "Assessment report: Dupixent" EMA/512262/2017 Committee for Medicinal Products for Human Use (CHMP) (100 pages) (Jul. 20, 2017).

Favrot et al. "A prospective study on the clinical features of chronic canine atopic dermatitis and its diagnosis" Veterinary Dermatology, 21:23-31 (2010).

Gavrilova, Tatyana "Immune Dysregulation in the Pathogenesis of Atopic Dermatitis" Dermatitis, 29:57-62 (2018).

GenBank Accession No. S26468 "Ig heavy chain V region—mouse" NCBI {2 pages) (Jul. 23, 1999).

Goel et al. "Plasticity within the Antigen-Combining Site May Manifest as Molecular Mimicry in the Humoral Immune Response" The Journal of Immunology, 173:7358-7367 {2004).

Grimstad et al. "Anti-interleukin-31-antibodies ameliorate scratching behavior in NC/Nga mice: a model of atopic dermatitis" Experimental Dermatology, 18:35-43 (2009).

Griot-Wenk et al. "Characterization of two dog IgE-specific antibodies elicited by different recombinant fragments of the epsilon chain in hens" Veterinary Immunology and Immunopathology, 64:15-32 (1998).

Gunneriusson et al. "Surface Display of a Functional Single-Chain Fv Antibody on Staphylococci" Journal of Bacteriology, 178(5):1341-1346 (1996).

Guttman-Yassky et al. "IL-17C: A Unique Epithelial Cytokine with Potential for Targeting across the Spectrum of Atopic Dermatitis and Psoriasis" Journal of Investigative Dermatology, 138:1467-1469 (2018).

Hammerberg et al. "Therapeutic anti-IgE monoclonal antibody single chain variable fragment (scFv) safety and immunomodulatory effects after one time injection in four dogs" Vet Dermatol., 28(1):52-e13 (2016).

Hammerberg et al. "Auto IgG anti-IgE and IgG X IgE Immune Complex Presence and Effects on ELISA-Based Quantitation of IgE in Canine Atopic Dermatitis, Demodectic Acariasis and Helminthiasis" Veterinary Immunology and Immunopathology, 60:33-46 (1997).

Hashiguchi et al. "Human FceRIa-Specific Human Single-Chain Fv (scFv) Antibody with Antagonistic Activity toward IgE/FceRIa-Binding" Journal of Biochemistry, 133(1):43-49 (2003).

Hawro et al. "Interleukin-31 does not induce immediate itch in atopic dermatitis patients and healthy controls after skin challenge" Allergy, 69:113-117 (2014).

Hunter et al. "Generation of canine-human Fc IgE chimeric antibodies for the determination of the canine IgE domain of interaction with FceRIa" Molecular Immunology, 45:2262-2268 (2008) (Abstract only).

Huston et al. "Protein engineering of antibody binding sites: Recovery of specific activity in an anti-digoxin single-chain Fv analogue

(56) References Cited

OTHER PUBLICATIONS produced in *Escherichia coli*" Proceedings of the National Academy of Sciences USA, 85:5879-5883 (1988).
Huston et al. "Protein Engineering of Single-Chain Fv Analogs and Fusion Proteins" Methods in Enzymology, 203:46-88 (1991) (Abstract only).
Jackson et al. "IgE is present on peripheral blood moncytes and B cells in normal dogs and dogs with atopic dermatitis but there is no correlation with serum IgE concentrations" Vet Immunol Immunopathol., 85(3-4):225-232 (2002).
Janeway et al. "Immunobiology: The Immune System in Health and Disease" Part II: The Recognition of Antigen, pp. 3:1-3:11 (1997).
Jones et al. "Replacing the complementarity-determining regions in a human antibody with those from a mouse" Nature, 321:522-525 (1986).
Kalina et al. "IgE ELISA Using Antisera Derived from Epsilon Chain Antigenic Peptides Detects Allergen-Specific IgE In Allergic Horses" Veterinary Immunology and Immunopathology, 92:137-147 (2003).
Kanyavuz et al. "Breaking the law: unconventional strategies for antibody diversification" Nature Reviews Immunology, 19:355-368 (2019).
Kostelny et al. "Formation of a bispecific antibody by the use of leucine zippers" Journal of Immunology, 148:1547-1553 (1992).
Kriangkum et al. "Bispecific and bifunctional single chain recombinant antibodies" Biomolecular Engineering, 18:31-40 (2001).
Kuby "Immunology" Second Edition, pp. 86-96 (1994).
Langan et al. "What Is Meant by a "Flare" in Atopic Dermatitis? A Systematic Review and Proposal" Archives of Dermatology, 142:1190-1196 (2006).
Lantto et al. "Chain Shuffling to Modify Properties of Recombinant Immunoglobulins" Methods in Molecular Biology, 178:303-316 (2002).
Lloyd et al. "Modelling the human immune response: performance of a 1011 human antibody repertoire against a broad panel of therapeutically relevant antigens" Protein Engineering, Design & Selection, 22(3):159-168 (2009).
Lourenco et al. "Efficacy of proactive long-term maintenance therapy of canine atopic dermatitis with 0.0584% hydrocortisone aceponate spray: a double-blind placebo controlled pilot study" Veterinary Dermatology, 27:88-e25 (2016).
Maddox et al. "Elevated Serum Levels in Human Pregnancy of a Molecule Immunochemically Similar to Eosinophil Granule Major Basic Protein" Journal of Experimental Medicine, 158:1211-1226 (1983).
Maniatis et al. "Regulation of Inducible and Tissue-Specific Gene Expression" Science, 236(4806):1237-1245 (1987).
Marks et al. "By-passing immunization: building high affinity human antibodies by chain shuffling" Biotechnology, 10(7):779-783 (1992).
Marsella et al. "Cellular and cytokine kinetics after epicutaneous allergen challenge (atopy patch testing) with house dust mites in high-IgE beagles" Veterinary Dermatology, 17:111-120 (2006).
Monino-Romero et al. "Soluble FcεRI: A biomarker for IgE-mediated diseases" Allergy, 74(7):1381-1384 (2019).
Morrison et al. "Chimeric human antibody molecules: mouse antigen-binding domains with human constant region domains" Proceedings of the National Academy of Sciences USA, 81:6851-6855 (1984).
Noda et al. "The Asian atopic dermatitis phenotype combines features of atopic dermatitis and psoriasis with increased TH17 polarization" Journal of Allergy and Clinical Immunology, 136(5):1254-1264 (2015).
Olivry et al. "Early Activation of Th2/Th22 Inflammatory and Pruritogenic Pathways in Acute Canine Atopic Dermatitis Skin Lesions" Journal of Investigative Dermatology, 136:1961-1969 (2016).
Olivry et al. "Investigations on the role of nerve growth factor in dogs with atopic dermatitis" Free Communication Abstracts: Friday Morning, Jun. 3, Session 8: Allergic Diseases: Pathobiology (Pathogenesis and Diagnosis) (FC54-62) (2016).

Olivry et al. "Stratum corneum removal facilitates experimental sensitization to mite allergens in atopic dogs" Veterinary Dermatology, 22:188-196 (2010).
Olivry et al. "Treatment of canine atopic dermatitis: 2015 updated guidelines from the international committee on allergic diseases of animals {ICADA}" BMC Veterinary Research, 11(210):1-15 (2015).
Orton et al. "Canine IgE Monoclonal Antibody Specific for a Filarial Antigen; Production by a Canine X Murine Heterohybridoma Using B Cells from a Clinically Affected Lymph Node" Immunology, 85(3):429-34 (1995).
Paps et al. "Development of an Allergen-induced Atopic Itch Model in Dogs: A Preliminary Report" Acta Dermato-Venereologica, 96:400-401 (2016).
Pucheu-Haston et al. "Review: Lymphocytes, cytokines, chemokines and the T-helper 1-T-helper 2 balance in canine atopic dermatitis" Veterinary Dermatology, 26:124-e32 (2015).
Riechmann et al. "Reshaping human antibodies for therapy" Nature, 332:323-327 (1988).
Rudikoff et al. "Single amino acid substitution altering antigen-binding specificity" Proceedings of the National Academy of Sciences, 79:1979-1983 (1982).
Songsivilai et al. "Bispecific antibody: a tool for diagnosis and treatment of disease" Clinical & Experimental Immunology, 79:315-321 (1990).
Steffan et al. "Remission of the clinical signs of atopic dermatitis in dogs after cessation of treatment with cyclosporin A or methylprednisolone" Veterinary Record, 154:681-684 (2004).
Takamori et al. "IL-31 is crucial for induction of pruritus, but not inflammation, in contact hypersensitivity" Scientific Reports, 8(6639):1-11 (2018).
Tamamoto-Mochizuki et al. "Proactive maintenance therapy of canine atopic dermatitis with the anti-IL-31 lokivetmab. Can a monoclonal antibody blocking a single cytokine prevent allergy flares?" Veterinary Dermatology, 30(2):98-e26 (2019).
Tang et al. "Are the concepts of induction of remission and treatment of subclinical inflammation in atopic dermatitis clinically useful?" Journal of Allergy and Clinical Immunology, 133:1615-1625 (2014).
Thomas et al. "Validation of Treatment Escalation as a Definition of Atopic Eczema Flares" PLoS One, 10(4):e0124770 (2015).
Tierney et al. "Tuberculosis (TB)" Merck Manuals Professional Edition, 14 pages; downloaded Mar. 22, 2021.
Vangelista et al. "A minimal receptor-Ig chimera of human FcεRI a-chain efficiently binds secretory and membrane IgE" Protein Engineering, Design and Selection, 15(1):51-57 (2002).
Verhoeyen et al. "Reshaping Human Antibodies: Grafting an Antilysozyme Activity" Science, 239(4847):1534-1536 (1988).
Vernersson et al. "Cloning, Structural Analysis, and Expression of the Pig IgE EChain" Immunogenetics, 46:461-468 (1997).
Voss et al. "The role of enhancers in the regulation of cell-type-specific transcriptional control" Trends in Biochemical Sciences, 11:287-289 (1986).
Ward et al. "Binding activities of a repertoire of single immunoglobulin variable domains secreted from *Escherichia coli*" Nature, 341:544-546 (1989).
Weidinger et al. "Atopic dermatitis" Nature Reviews Disease Primers, 4(1):1-20 (2018).
Welcome to UniCAP® InvitroSight(TM) version 3.1, an Interactive Allergy Testing Information and Know-How Service from Pharmacia Diagnostics Pharmacia Diagnostics AB, 7 pages (2002).
Wilhelm et al. "Breed-associated phenotypes in canine atopic dermatitis" Veterinary Dermatology, 22:143-149 (2010).
William H. Wong, Ph.D. "Allergen Specific IgE" Technical Bulletin, Diagnostic Laboratory Services Inc., 7 pages (1996).
Al Qaraghuli et al. "Antibody-protein binding and conformational changes: identifying allosteric signalling pathways to engineer a better effector response" Scientific Reports, 10(13696) (10 pages) (2020).
Bhattacharya et al. "Impact of genetic variation on three dimensional structure and function of proteins" PLoS One, 12(3):e0171355 (2017).

(56) References Cited

OTHER PUBLICATIONS

Fenton et al. "Rheostat positions: A new classification of protein positions relevant to pharmacogenomics" Medicinal Chemistry Research, 29:1133-1146 (2020).
Guo et al. "Protein tolerance to random amino acid change" PNAS, 101(25):9205-9210 (2004).
Mantovani et al. "Decoy receptors: a strategy to regulate inflammatory cytokines and chemokines" Trends in Immunology, 22(6):328-336 (2001).
Tokuriki et al. "Stability effects of mutations and protein evolvability" Current Opinion in Structural Biology, 19:596-604 (2009).
Bachmann et al. "Vaccination against IL-31 for the treatment of atopic dermatitis in dogs" Journal of Allergy and Clinical Immunology, 142(1):279-281 (2018).
Janeway, C. et al. "Part II: The Recognition of Antigen" in: Immuno Biology The Immune System in Health and Disease Third Edition (Current Biology Ltd./Garland Publishing Inc., London, New York, 1997), pp. 3:1-3:11.
Kuby, Janis "Antigens" in: Immunology Second Edition (W. H. Freeman and Company, New York, 1994), pp. 85-96.
Wenzel et al. "Dupilumab efficacy and safety in adults with uncontrolled persistent asthma despite use of medium-to-high-dose inhaled corticosteroids plus a long-acting ß2 agonist" Lancet, 388:31-44 (2016).

\* cited by examiner

5' GG CGC GCC ACC ATG GAG ACA GAC ACA CTC CTG CTA TGG GTA CTG CTC TGG GTT CCA GGT TCC ACT GGT GAC GAG GTG CAG CTT CAG GAG TCA GGA CCT AGC CTC GTG AAA CCT TCT CAG ACT CTG TCC CTC ACC TGT TCT GTC ACT GGC GAC TCC ATC ACC AGT GGT TTC TGG AAC TGG ATC CGG AAA TTC CCA GGG AAT AAA CTT GAG TAC ATG GGT TAC ATA AGC TAC AGT GGT AGC ACT TAC TAC AAT CCA TCT CTC AAA AGT CGA ATC TCC ATC ACT CGA GAC ACA TCC AAG AAC CAG TAC TAC CTA CAG TTG AAT TCT GTG ACT ACT GCG GAC ACA GCC ACA TAT TAC TGT GCA AGA GGG GAT ATG AGG TAC AAC GCC TGG TTT GCT TAC TGG GGC CAA GGG ACT CTG GTC TCT GCA GGA GGT GGA GGT TCT GGA GGT GGA GGT TCA GGA GGT GGA GGT AGT GAT GTT GTG ATG ACC CAA ACT CCA CTC TCC CTG CCT GTC AGT CTT GGA GAT CAA GCC TCC ATC TCT TGC AGA TCT AGT CAG AGC CTT GTA CAC AGT AAT GGA AAC ACC TAT TTA CAT TGG TAC CTG CAG AAG CCA GGC CAG TCT CCA AAG CTC CTG ATC TAC AAA GTT TCC AAC CGA TTT TCT GGG GTC CCA GAC AGG TTC AGT GGC AGT GGA TCA GGG ACA GAT TTC ACA CTC AAG ATC AGC AGA GTG GAG GCT GAG GAT CTG GGA GTT TAT TTC TGC TCT CAA AGT ACA CAT GCT CCT CCC ACG TTC GGA GGG GGG ACC AAG CTG GAA ATA AAA TAA GCGGCCGC -3' [SEQ ID NO: 13]

Fig. 1

METDTLLLWVLLLWVPGSTGDEVQLQESGPSLVKPSQTLSLTCSVTGDSITSGFWNWIRKFPGNKLEYMGYISYSG STYYNPSLKSRISITRDTSKNQYYLQLNSVTTADTATYYCARGDMRYNAWFAYWGQGTLVTVSAGGGSGGGGS GGGGSDVVMTQTPLSLPVSLGDQASISCRSSQSLVHSNGNTYLHWYLQKPGQSPKLLIYKVSNRFSGVPDRFSGSG SGTDFTLKISRVEAEDLGVYFCSQSTHAPPTFGGGTKLEIK [SEQ ID NO: 12]

Fig. 2

METHODS AND COMPOSITIONS FOR ANTIBODY TO HIGH AFFINITY RECEPTOR FOR IgE

STATEMENT OF PRIORITY

This application claims the benefit, under 35 U.S.C. § 119(e), of U.S. Provisional Application Ser. No. 62/647,385, filed Mar. 23, 2018, the entire contents of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 5051-936_ST25.txt, 8,914 bytes in size, generated on Dec. 1, 2020 and filed via EFS-Web, is provided in lieu of a paper copy. This Sequence Listing is hereby incorporated herein by reference into the specification for its disclosure.

FIELD OF THE INVENTION

The present invention is directed to an antibody that specifically binds an IgE receptor and methods of its use.

BACKGROUND OF THE INVENTION

Allergic disorders are currently the 6th leading cause of chronic illness in the U.S. and are steadily increasing every year. Studies have shown that as many as 30% of adults and 40% of children in the U.S. are currently afflicted with an allergic disorder. Allergic disorders also account for about 25% of all visits to the veterinarian for dogs and cats. For example, canine atopic dermatitis in dogs is the second most common allergic skin condition affecting about 10-15% of animals.

Allergic disorders in humans as well as dogs and cats have been primarily linked to the exposure to specific allergens, such as dust mites, pollen, dander, latex, insect venoms, medicines or certain foods (e.g., milk, peanuts, eggs, and shellfish). Medications currently prescribed for treating allergic disorders vary depending on the allergic disorder and corresponding symptoms being treated.

Risk assessments currently practiced in veterinary and human medicine for allergic disorders is primarily based on serological measurements of total IgE and allergen-specific IgE. Unfortunately such measurements have been demonstrated to lack a strong correlation to clinical allergic disease presentation. Recent studies suggest that the extensive network of serum proteins present in blood can associate with serum IgE. Thus, the current methods of diagnosis of allergic disease by measurements of total and allergen-specific IgE in serum have been limited by the inability to differentiate many serum factors that bind to IgE.

The present invention overcomes previous shortcomings in the art by providing an antibody that specifically binds an IgE high affinity receptor and methods of its use.

SUMMARY OF THE INVENTION

In one aspect, the present invention provides an antibody that binds to IgE high affinity receptor (FcεRIα) at an epitope within the amino acid sequence CNGNNFFEVSSTKWFHNGS (SEQ ID NO:1) of human FcεRIα or at an epitope within the corresponding amino acid sequence of a different mammalian species. In some embodiments, the antibody of the invention binds to canine FcεRIα at an epitope within the amino acid sequence CTGNNSLEVDSAVWLHNNT (SEQ ID NO:2). In some embodiments, the antibody of the invention binds to equine FcεRIα at an epitope within the amino acid sequence CNKNKPLKGNSTEWTYNNT (SEQ ID NO:3). In some embodiments, the antibody of the invention is a single chain variable fragment (scFv).

In a further aspect, the present invention provides a recombinant nucleic acid molecule encoding the antibody of this invention.

In another aspect, the present invention provides a method of guiding treatment in a subject in need thereof, comprising the steps of administering an anti-IgE treatment to the subject; and measuring a level of IgE high affinity receptor on monocytes in a sample from the subject by contacting the sample with the antibody of this invention and detecting the level of IgE high affinity receptor on monocytes in the sample, wherein the level≥a threshold value identifies the subject as needing modification of the administered IgE treatment and/or needing an alternate treatment therapy.

The invention additionally provides a method of guiding treatment in a subject in need thereof, comprising the steps of administering an anti-IgE treatment to the subject; and measuring a level of free IgE high affinity receptor in a sample from the subject by contacting the sample with the antibody of this invention and detecting the level of free IgE high affinity receptor in the sample, wherein the level≥a threshold value identifies the subject as needing modification of the administered IgE treatment and/or needing an alternate treatment therapy.

The present invention is explained in greater detail in the drawings herein and the specification set forth below. The disclosures of all patent and nonpatent publications and references cited herein are incorporated by reference herein in their entirety.

BRIEF DESCRIPTION OF THE DRAWINGS

FIG. 1. Nucleotide sequence of anti-canine FcεRIα scFv construct (SEQ ID NO:13).

FIG. 2. Amino Acid Sequence of anti-canine FcεRIα scFv construct (SEQ ID NO:12).

DETAILED DESCRIPTION OF THE INVENTION

Figure 3:
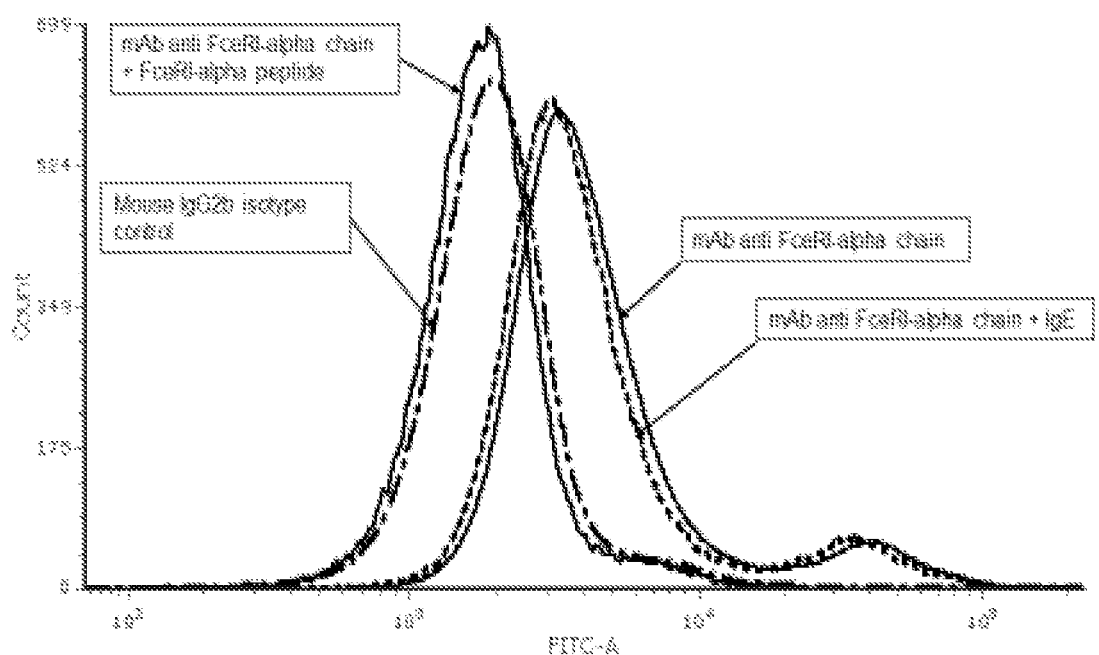
FIG. 3. Results of flow cytometry of monoclonal antibody (mAb) anti-FcεRIα with canine mast cells with/without IgE.

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for cloning genes, amplifying and detecting nucleic acids, and the like. Such techniques are known to those skilled in the art. See, e.g., Sambrook et al., Molecular Cloning: A Laboratory Manual 2nd Ed. (Cold Spring Harbor, NY, 1989); Ausubel et al. Current Protocols in Molecular Biology (Green Publishing Associates, Inc. and John Wiley & Sons, Inc., New York).

All publications, patent applications, patents, patent publications and other references cited herein are incorporated by reference in their entireties for the teachings relevant to the sentence and/or paragraph in which the reference is presented.

The invention, in part, relates to compositions and methods for treating allergic disorders and/or guiding anti-IgE treatment therapy using an antibody of this invention. The general mechanism of allergic diseases and disorders begins with sensitization. When, for example, allergens are exposed to antigen presenting cells in the body, such antigens are internalized, processed and then expressed on the cell surface of the antigen presenting cells. The allergens are then presented to other cells involved in an immune response, particularly T-lymphocytes. Through a series of specific cell interactions B-lymphocytes are transformed into antibody secretory cells—plasma cells. In the initial allergic response, the plasma cell produces IgE-antibodies, which, like antibodies of other immunoglobulin isotypes, are capable of binding a specific allergen via its Fab portion. Different allergens stimulate the production of corresponding allergen-specific IgE antibodies. Once formed and released into the circulation, IgE binds, through its Fc portion, to a high affinity receptor on mast cells, leaving its allergen specific receptor site available for future interaction with allergen. Production of allergen specific IgE-antibodies completes the immune response known as sensitization.

Subsequent exposure to the same allergen is typically associated with an inflammatory response, which, in part, is the cause for some of the symptoms experienced by patients afflicted with an allergic disease or disorder. In general, this inflammatory response is due to the body's reaction toward a second exposure of an allergen triggering an inflammatory cascade. The inflammatory cascade consists of an early phase inflammatory reaction and a late phase inflammatory reaction. The early phase inflammatory reaction occurs within minutes of allergen exposure and mainly reflects the secretion of mediators by mast cells at the affected site. In sensitized individuals, these mast cells already have allergen-specific IgE bound to their surface high-affinity IgE receptors (FcεRI). IgE does not only bind to this receptor but also has the ability upregulate the expression of FcεRI as well as promote aggregation of this receptor. A subsequent exposure to the same allergen cross-links the cell-bound IgE and triggers the release of pre-formed inflammatory mediators which contribute to the acute signs and symptoms associated with early phase inflammatory response. In the late phase inflammatory reaction, mast cells responding to IgE and allergen also release a broad range of newly synthesized cytokines, chemokines, and growth factors, but they are released more slowly than the pre-formed inflammatory mediators and contribute to the signs and symptoms associated with late phase inflammatory response.

The efficacy of current treatments for allergic disorders, particularly anti-IgE treatment therapy, primarily relies on the measurements of serum levels of total IgE and allergen-specific IgE. A reduction in serum levels of total IgE and allergen-specific IgE is currently considered an indicator that the current therapy appears to be effective in treating allergic inflammation. However, as mentioned above, current methods for measuring IgE levels, particularly "free" IgE levels, are limited due to interfering interactions of other constituents present in serum that also associate with IgE.

Thus, one aspect, the present invention is based on the discovery and development of a diagnostic composition for monitoring and/or guiding treatment of allergic disorders using an antibody of this invention. Binding of the antibody to an identified epitope on the FcεRI alpha chain allows for detection of FcεRI free or complexed with IgE in serum, and thus, FcεRI can be detected on cells in the presence or absence of IgE. Since IgE levels can modulate the expression level of FcεRI, measuring the concentration of this receptor in the presence or absence of IgE provides an improved biomarker for correlating clinical manifestations in allergic subjects, particularly as FcεRI measurements do not suffer from any interfering cellular interactions that would result in inaccurate measurements of the receptor. Thus, measuring the level of FcεRI in free form and/or on monocytes in a sample taken from a subject afflicted with an allergic disorder currently receiving an anti-IgE treatment provides valuable information as to the efficacy of the anti-IgE treatment.

In some embodiments, the measured level of FcεRI in free form and/or on monocytes can be equal to or above a threshold value indicating that the administered anti-IgE treatment needs modifications (e.g., increase or decrease in dose, modifications of frequency of administration, and/or route of administration) and/or that an alternate treatment therapy may be required (e.g., addition of a second therapeutic agent to the current anti-IgE treatment and/or administration of one or more different therapeutic agents (e.g., anti-inflammatory agents such as steroids including corticosteroids, immunomodulatory agents, non-steroidal anti-inflammatory agents, anti-prostaglandin agents, anti-IgE agents, and any combination thereof)). In some embodiments, the measured level of FcεRI in free form and/or on monocytes can be below a threshold value, indicating that the currently administered anti-IgE treatment is effective in reducing inflammation and does not need to be modified and/or can be maintained or discontinued.

Another aspect of the invention relates to a therapeutic composition comprising an antibody of this invention that binds an epitope site on the alpha chain (of dogs, horses, and humans) that blocks the IgE cross-FcεRI linking event described above. Such a blockage would inhibit the release of pre-formed inflammatory mediators occurring in the early phase during inflammation and thus would provide a reduction in FcεRI cross-linking in inflammatory cells, thereby reducing the severity of clinical manifestation associated with early phase inflammatory response observed in allergic subjects.

Another aspect of the invention relates to the linkage of an anti-FcεRIα antibody fragment to an anti-IgGγRIIb antibody fragment, to inhibit FcεRIα-bearing inflammatory cells from contributing to allergic inflammation. Thus, in some embodiments, the invention provides a chimeric protein comprising an anti-FcεRIα antibody fragment linked to an anti-IgGγRIIb antibody fragment in methods for inhibiting/preventing/treating allergic inflammation and/or an allergic disorder.

Thus, in one embodiment, the present invention provides an antibody that binds to FcεRIα at an epitope within the amino acid sequence CNGNNFFEVSSTKWFHNGS (SEQ ID NO:1) of human FcεRIα or at an epitope within the corresponding amino acid sequence of a different mammalian species. In some embodiments, the antibody of this invention binds to canine FcεRIα at an epitope within the amino acid sequence CTGNNSLEVDSAVWLHNNT (SEQ ID NO:2). In some embodiments, the antibody of this invention binds to equine FcεRIα at an epitope within the amino acid sequence CNKNKPLKGNSTEWTYNNT (SEQ ID NO:3). In some embodiments, the antibody of this invention is a single chain variable fragment (scFv).

In a further embodiment, the present invention provides an antibody, wherein the antibody is a scFv that comprises (i) a light chain (LC) variable region having at complementarity determining regions (CDRs) thereof at least one, two, or all three, in any combination, of the amino acid sequences: RSSQSLVHSNGNTYLH (LC CDR1; SEQ ID NO:4); KVSNRFS (LC CDR2; SEQ ID NO:5); and SQSTHAPPT (LC CDR3; SEQ ID NO:6); and/or (ii) a heavy chain (HC) variable region having at complementarity determining regions (CDRs) thereof at least one, two, or all three, in any combination, of the amino acid sequences: SGFWN (HC CDR1; SEQ ID NO:7); YISYSGSTYYNPSLKS (HC CDR2; SEQ ID NO:8); and GDMRYNAWFAY (HC CDR3; SEQ ID NO:9).

In some embodiments, the scFv can comprise, consist essentially of or consisting of the amino acid sequence:

```
                                         (SEQ ID NO: 14)
METDTLLLWVLLLWVPGSTGDEVQLQESGPSLVKPSQTLSLTCSVTGDS

ITSGFWNWIRKFPGNKLEYMGYISYSGSTYYNPSLKSRISITRDTSKNQ

YYLQLNSVTTADTATYYCARGDMRYNAWFAYWGQGTLVTVSA

-a linker sequence-
                                         (SEQ ID NO: 10)
DVVMTQTPLSLPVSLGDQASISCRSSQSLVHSNGNTYLHWYLQKPGQSP

KLLIYKVSNRFSGVPDRFSGSGSGTDFTLKISRVEAEDLGVYFCSQSTH

APPTFGGGTKLEIK.
```

In some embodiments, the linker sequence can comprise (GGGS)n subunits in any combination and n can be 1 or any number greater than 1 (e.g., 2, 3, 4, 5, 6, 7, 8, 9, 10, 11, 12, 13, 14, 15, 16, 17, 18, 19, 20, 25, 30, 35, 40, 45, 50, etc). In some embodiments, the linker peptide can comprise, consist essentially of, or consist of the amino acid sequence: GGGGSGGGGSGGGGS (SEQ ID NO:11). In some embodiments, the scFv is humanized, caninized, felinized, or equinized according to protocols know in the art.

In some embodiments, the scFv can comprise, consist essentially of or consisting of the amino acid sequence:

```
                                         (SEQ ID NO: 12)
METDTLLLWVLLLWVPGSTGDEVQLQESGPSLVKPSQTLSLTCSVTGDS

ITSGFWNWIRKFPGNKLEYMGYISYSGSTYYNPSLKSRISITRDTSKNQ

YYLQLNSVTTADTATYYCARGDMRYNAWFAYWGQGTLVTVSAGGGGSGG

GGSGGGGSDVVMTQTPLSLPVSLGDQASISCRSSQSLVHSNGNTYLHWY

LQKPGQSPKLLIYKVSNRFSGVPDRFSGSGSGTDFTLKISRVEAEDLGV

YFCSQSTHAPPTFGGGTKLEIK
```

In some embodiments of this invention, the antibody can further comprise a water soluble polyalkylene oxide group or moiety coupled thereto. In particular embodiments, the water soluble polyalkylene oxide group can comprise polyethylene glycol (i.e., the antibody can be "pegylated"). The polyalkylene glycol moiety can be linked or attached or associated with the antibody at either or both ends of the protein.

In some embodiments, the scFv of this invention can form an antigen-binding monomer.

The present invention further provides a composition comprising the antibody of this invention in a pharmaceutically acceptable carrier.

In another embodiment of this invention, a recombinant nucleic acid molecule (e.g., an isolated recombinant nucleic acid molecule) is provide, which encodes the antibody of this invention. Also provided herein is a composition comprising the recombinant nucleic acid molecule of this invention in a pharmaceutically acceptable carrier.

The present invention additionally provides a host cell containing the recombinant nucleic acid molecule of this invention. In some embodiments, the host cell expresses the nucleic acid molecule to produce the encoded antibody.

The host cell of this invention can be a bacterial cell, a yeast cell, a mammalian cell, or a plant cell.

The present invention further comprises methods of guiding treatment in a subject in need thereof, comprising the steps of administering an anti-IgE treatment to the subject; and measuring a level of IgE high affinity receptor on monocytes in a sample from the subject by contacting the sample with the antibody of this invention and detecting the level of IgE high affinity receptor on monocytes in the sample, wherein the level≥a threshold value identifies the subject as needing modification of the administered IgE treatment and/or needing an alternate treatment strategy.

The present invention additionally provides a method of guiding treatment in a subject in need thereof, comprising the steps of administering an anti-IgE treatment to the subject; and measuring a level of free IgE high affinity receptor in a sample from the subject by contacting the sample with the antibody of this invention and detecting the level of free IgE high affinity receptor in the sample, wherein the level≥a threshold value identifies the subject as needing modification of the administered IgE treatment and/or needing an alternate treatment strategy.

In some embodiments, the methods of this invention further comprise the step of administering a modified IgE treatment and/or administering an alternate treatment regiment to the subject.

A threshold value can be a pre-determined value or a value for each specific assay and in some embodiments can be, e.g., a positive and/or negative control value. For example, a control value can be a predetermined or concurrently generated value or range of values based on measurements taken from one or more subjects not afflicted with an allergic disorder. Another example of a control value is a value or range of values based on measurements taken from one or more subjects afflicted with an allergic disorder not receiving treatment. In some embodiments, a threshold value ranges from about 100 MFI to about 1,000 MFI (Median Fluorescence Intensity), from about 100 MFI to about 750 MFI, from about 100 MFI to about 500 MFI, or from about 100 MFI to about 250 MFI. In some embodiments, the threshold value is 100 MFI, 200 MFI, 300 MFI, 400 MFI, 500 MFI, 600 MFI, 700 MFI, 800 MFI, 900 MFI, or 1,000 MFI. In some embodiments, a threshold value ranges from about 0.5 µg/mL to about 100 µg/mL, from about 0.5 µg/mL to about 75 µg/mL, from about 0.5 µg/mL to about 55 µg/mL, from about 0.75 µg/mL to about 35 µg/mL, or from about 0.80 µg/mL to about 20 µg/mL.

The terms "a," "an" and "the" are used herein to refer to one or to more than one (i.e., at least one) of the grammatical object of the article. By way of example, "an element" means at least one element and can include more than one element (e.g., a multiplicity or plurality of elements).

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, "one or more" can mean one, two, three, four, five, six, seven, eight, nine, ten or more, up to any number.

As used herein, the term "subject" and "patient" are used interchangeably herein and refer to both human and nonhuman animals. A subject of this invention can be any subject that is susceptible to an allergic disorder and in particular embodiments; the subject of this invention is a human subject.

A "subject in need thereof" or "a subject in need of" is a subject known to have, or is suspected of having or developing or is a subject at increased risk for having or developing an allergic disorder.

An "appropriate therapy" for the treatment of an allergic disorder of this invention includes therapies well known in the art, including but not limited to, anti-inflammatory agents, anti-IgE agents, immunomodulatory agents, and any combination thereof.

The term "administering" or "administered" as used herein is meant to include topical, parenteral and/or oral administration, all of which are described herein. Parenteral administration includes, without limitation, intravenous, subcutaneous and/or intramuscular administration (e.g., skeletal muscle or cardiac muscle administration). It will be appreciated that the actual method and order of administration will vary according to, inter alia, the particular preparation of compound(s) being utilized, and the particular formulation(s) of the one or more other compounds being utilized. The optimal method and order of administration of the compounds of the invention (e.g., compounds directed towards anti-IgE treatment) for a given set of conditions can be ascertained by those skilled in the art using conventional techniques and in view of the information set out herein.

The term "administering" or "administered" also refers, without limitation, to oral, sublingual, buccal, transnasal, transdermal, rectal, intramuscular, intravenous, intraarterial (intracoronary), intraventricular, intrathecal, and subcutaneous routes. In accordance with good clinical practice, the instant compounds can be administered at a dose that will produce effective beneficial effects without causing undue harmful or untoward side effects, i.e., the benefits associated with administration outweigh the detrimental effects.

Also as used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, and/or change in clinical parameters of the condition, disorder, disease or illness, etc., as would be well known in the art.

Additionally as used herein, the terms "prevent," "preventing" or "prevention" refer to any type of action that results in the absence, avoidance and/or delay of the onset and/or progression of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the methods of the present invention.

An "effective amount" or "therapeutically effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, *The Science and Practice of Pharmacy* (latest edition)).

The term "biologically active" as used herein means an enzyme or protein having structural, regulatory, or biochemical functions of a naturally occurring molecule.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed.

Subjects with which the present invention is concerned include any subject susceptible to an allergic condition or disorder and are, in general, mammalian subjects, including humans, dogs, cats, and horses. The subjects may be of any gender, any ethnicity and any age.

"Therapeutically effective amount" or "treatment effective amount" or "effective amount" as used herein refers to the amount of an anti-IgE agent determined to produce a therapeutic response in a mammal. Such therapeutically effective amounts are readily ascertained by one of ordinary skill in the art.

"Antibody" as used herein refers to an intact immunoglobulin of any isotype, or a fragment thereof that can compete with the intact antibody for specific binding to the target antigen, and includes chimeric, humanized, caninized, equinized, felinized, fully human, fully canine, fully equine, fully feline, and bispecific antibodies. An intact antibody generally will comprise at least two full-length heavy chains and two full-length light chains, but in some instances may include fewer chains such as antibodies naturally occurring in camelids which may comprise only heavy chains. Antibodies according to the invention may be derived solely from a single source, or may be "chimeric," that is, different portions of the antibody may be derived from two different antibodies. For example, the CDR regions may be derived from a rat or murine source, while the framework region of the V region is derived from a different animal source, such as a human. The antibodies or binding fragments of the invention may be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below.

"Light chain" as used herein includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains according to the invention include kappa chains and lambda chains.

"Heavy chain" includes a full-length heavy chain and fragments thereof having sufficient variable region sequence to confer binding specificity. A full-length heavy chain includes a variable region domain, $V_H$, and three constant region domains, $C_{H1}$, $C_{H2}$, and $C_{H3}$. The $V_H$ domain is at the amino-terminus of the polypeptide, and the $C_H$ domains are at the carboxyl-terminus, with the $C_{H3}$ being closest to the —COOH end. Heavy chains according to the invention may be of any isotype, including IgG (including IgG1, IgG2, IgG3 and IgG4 subtypes), IgA (including $IgA_1$ and $IgA_2$ subtypes), IgM and IgE.

"Immunologically functional fragment" (or simply "fragment") of an immunoglobulin chain, as used herein, refers to a portion of an antibody light chain or heavy chain that lacks at least some of the amino acids present in a full-length chain but which is capable of binding specifically to an antigen. Such fragments are biologically active in that they bind specifically to the target antigen and can compete with intact antibodies for specific binding to a given epitope. In one aspect of the invention, such a fragment will retain at least one CDR present in the full-length light or heavy chain, and in some embodiments will comprise a single heavy chain and/or light chain or portion thereof. These biologically active fragments may be produced by recombinant DNA techniques, or may be produced by enzymatic or chemical cleavage of intact antibodies. Immunologically functional immunoglobulin fragments of the invention include, but are not limited to, Fab, Fab', $F(ab')_2$, Fv, domain antibodies and single-chain antibodies, and may be derived from any mammalian source, including but not limited to human, mouse, rat, camelid or rabbit. It is contemplated further that a functional portion of the inventive antibodies, for example, one or more CDRs, could be covalently bound to a second protein or to a small molecule to create a therapeutic agent directed to a particular target in the body, possessing bifunctional therapeutic properties, or having a prolonged serum half-life.

"Fab fragment" as used herein is comprised of one light chain and the CHI and variable regions of one heavy chain. The heavy chain of a Fab molecule cannot form a disulfide bond with another heavy chain molecule.

"Fc" region as used herein contains two heavy chain fragments comprising the $C_{H1}$ and $C_{H2}$ domains of an antibody. The two heavy chain fragments are held together by two or more disulfide bonds and by hydrophobic interactions of the CH3 domains.

"Fab' fragment" contains one light chain and a portion of one heavy chain that contains the $V_H$ domain and the $C_{H1}$ domain and also the region between the $C_{H1}$ and $C_{H2}$ domains, such that an interchain disulfide bond can be formed between the two heavy chains of two Fab' fragments to form a $F(ab')_2$ molecule.

"$F(ab')_2$ fragment" contains two light chains and two heavy chains containing a portion of the constant region between the $C_{H1}$ and $C_{H2}$ domains, such that an interchain disulfide bond is formed between the two heavy chains. A $F(ab')_2$ fragment thus is composed of two Fab' fragments that are held together by a disulfide bond between the two heavy chains.

"Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203, the disclosures of which are incorporated by reference.

"Domain antibody" as used herein is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

"Bivalent antibody" as used herein comprises two antigen binding sites. In some instances, the two binding sites have the same antigen specificities. However, bivalent antibodies may be bispecific (see below).

"Multispecific antibody" as used herein is one that targets more than one antigen or epitope.

"Bispecific," "dual-specific" or "bifunctional" antibody as used herein is a hybrid antibody having two different antigen binding sites. Bispecific antibodies are a species of multispecific antibody and may be produced by a variety of methods including, but not limited to, fusion of hybridomas or linking of Fab' fragments. See, e.g., Songsivilai & Lachmann (1990), Clin. Exp. Immunol. 79:315-321; Kostelny et al. (1992), J. Immunol. 148:1547-1553. The two binding sites of a bispecific antibody will bind to two different epitopes, which may reside on the same or different protein targets.

As discussed herein, a variety of selective binding agents useful for regulating the activity of IgE are provided. These agents include, for instance, antibodies and immunologically functional fragments thereof that contain an antigen binding domain (e.g., single chain antibodies, domain antibodies, immunoadhesions, and polypeptides with an antigen binding region) and specifically bind to the IgE high affinity receptor (FCεRI).

Variable Domains of Antibodies. Also provided are antibodies that comprise a light chain variable region as described herein, and/or a heavy chain variable region as described herein CDRs of Antibodies. The antibodies and immunological functional fragments that are provided can include one or more complementarity determining regions (CDRs) (e.g., one, two, three, four, five or all six CDRs). The heavy and light chain variable regions and the CDRs that are disclosed herein can be used to prepare any of the various types of immunologically functional fragments that are known in the art including, but not limited to, domain antibodies, Fab fragments, Fab' fragments, F(ab)$_2$ fragments, Fv fragments, single-chain antibodies, sdFvs, scFvs, etc.

Single-chain Variable Fragments. Single chain variable fragment (scFv) antibodies can be produced in accordance with known techniques or variations thereof that will be apparent to those skilled in the art. See generally U.S. Pat. No. 4,946,778 to Ladner et al. and 5,258,498 to Huston and Opperman; see also U.S. Pat. Nos. 8,097,704; 8,043,830; 7,943,144; 7,910,702; and 7,816,334.

Bispecific or Bifunctional Antibodies. The antibodies that are provided also include bispecific and bifunctional antibodies that include one or more CDRs or one or more variable regions as described above. A bispecific or bifunctional antibody in some instances is an artificial hybrid antibody having two different heavy/light chain pairs and two different binding sites. Bispecific antibodies may be produced by a variety of methods including, but not limited to, fusion of hybridomas or linking of Fab' fragments. See, e.g., Songsivilai & Lachmann, 1990, Clin. Exp. Immunol. 79: 315-321; Kostelny et al., 1992, J. Immunol. 148: 1547-1553.

Chimeric, Humanized, Caninized, Equinized, and Felinized Antibodies. Chimeric and humanized antibodies based upon the foregoing sequences are also provided. Monoclonal antibodies for use as diagnostic agents may be modified in various ways prior to use. One example is a "chimeric" antibody, which is an antibody composed of protein segments from different antibodies that are covalently joined to produce functional immunoglobulin light or heavy chains or immunologically functional portions thereof. Generally, a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. For methods relating to chimeric antibodies, see, for example, U.S. Pat. No. 4,816,567; and Morrison et al., Proc. Natl. Acad. Sci. USA 81:6851-6855 (1985), which are hereby incorporated by reference. CDR grafting is described, for example, in U.S. Pat. Nos. 6,180,370, 5,693, 762, 5,693,761, 5,585,089, and 5,530,101, which are all hereby incorporated by reference for all purposes.

Generally, the goal of making a chimeric antibody is to create a chimera in which the number of amino acids from the intended patient species is maximized. One example is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the V region or selected CDRs from a rodent antibody often are grafted into a human antibody, replacing the naturally-occurring V regions or CDRs of the human antibody.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent variable region for the corresponding regions of a human antibody (see, e.g., U.S. Pat. Nos. 5,585,089, and 5,693,762; Jones et al., 1986, Nature 321:522-25; Riechmann et al., 1988, Nature 332:323-27; Verhoeyen et al., 1988, Science 239: 1534-36).

Caninized, equinized, and felinized antibodies are known, and are made in like manner as described in connection with humanized antibodies above. See, e.g., U.S. Pat. Nos. 8,076, 456; 7,261,890; 6,881,557; 6,504,013; 5,760,185; and US Patent Application Pub. No. US 2010/0061988.

In one aspect of the invention, the CDRs of the light and heavy chain variable regions of the antibodies provided herein are grafted to framework regions (FRs) from antibodies from the same, or a different, phylogenetic species. For example, the CDRs of the light and heavy chain variable regions of the antibody can be grafted to consensus human, canine, equine, or feline FRs. To create consensus FRs, FRs from several heavy chain or light chain amino acid sequences of the desired species may be aligned to identify a consensus amino acid sequence. In other embodiments, the FRs of the antibody heavy chain or light chain are replaced with the FRs from a different heavy chain or light chain.

In one aspect of the invention, rare amino acids in the FRs of the heavy and light chains of the chimeric protein are not replaced, while the rest of the FR amino acids are replaced. A "rare amino acid" is a specific amino acid that is in a position in which this particular amino acid is not usually found in an FR. Alternatively, the grafted variable regions from the antibody may be used with a constant region that is different from the constant region of. In other embodiments of the invention, the grafted variable regions are part of a single chain Fv antibody.

Nucleic acid molecules that encode an antibody of this invention, one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing are also provided. The nucleic acid molecules can be any length, and/or can comprise one or more additional sequences, for example, regulatory sequences, and/or be part of a larger nucleic acid molecule, for example, a vector. The nucleic acid molecules can be single-stranded or double-stranded and can comprise RNA and/or DNA nucleotides, and artificial variants thereof (e.g., peptide nucleic acids). In some embodiments, the nucleic acid molecules can be present in a composition comprising a pharmaceutically acceptable carrier and can be used in the methods of this invention for therapeutic applications.

In another aspect, the present invention provides vectors comprising a nucleic acid encoding a polypeptide of the invention or a portion thereof (e.g., a fragment containing one or more CDRs or one or more variable region domains). Examples of vectors include, but are not limited to, plasmids, viral vectors, non-episomal mammalian vectors and expression vectors, for example, recombinant expression vectors, Tumor-inducing (Ti) plasmids, ballistic particles carrying recombinant nucleic acids, etc. The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, Trends Biochem. Sci. 11:287, Maniatis et al., 1987, Science 236:1237, incorporated by reference herein in their entireties), and those that direct inducible expression of a nucleotide sequence in response to particular treatment or condition (e.g., the metallothionein promoter in mammalian cells and the tet-responsive and/or streptomycin responsive promoter in both prokaryotic and eukaryotic systems. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell (for example, *E. coli*) or eukaryotic cell (for example, yeast, insect, plant, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

A single chain antibody of the present invention may be formed by linking heavy and light chain variable domain (Fv region) fragments via an amino acid bridge (short peptide linker), resulting in a single polypeptide chain. Such single-chain Fvs (scFvs) may be prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains. By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci.* USA 85:5879; Ward et al., 1989, *Nature* 334:544, de Graaf et al., 2002, *Methods Mol Biol.* 178:379-87.

Antibodies provided herein that are of one subclass can be changed to antibodies from a different subclass using subclass switching methods. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See, e.g., Lantto et al., 2002, *Methods Mol. Biol.* 178:303-16.

Moreover, techniques for deriving antibodies having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al., 1992, *BioTechnology*, 10:779.

Conservative modifications may be made to the heavy and light chains described herein (and corresponding modifications to the encoding nucleic acids) to produce a chimeric protein having functional and biochemical characteristics. Methods for achieving such modifications are described herein.

Antibodies and functional fragments thereof according to the invention may be further modified in various ways. For example, if they are to be used for diagnostic purposes, they may be conjugated with polyethylene glycol (pegylated) to prolong the serum half-life or to enhance protein delivery. Alternatively, the V region of the subject antibodies or fragments thereof may be fused with the Fc region of a different antibody molecule. The Fc region used for this purpose may be modified so that it does not bind complement, thus reducing the likelihood of inducing cell lysis in the patient when the antibody is used as a diagnostic agent. In addition, the subject antibodies or functional fragments thereof may be conjugated with human serum albumin to enhance the serum half-life of the antibody or fragment thereof. Another useful fusion partner for the inventive antibodies or fragments thereof is transthyretin (TTR). TTR has the capacity to form a tetramer, thus an antibody-TTR fusion protein can form a multivalent antibody which may increase its binding avidity.

Alternatively, substantial modifications in the functional and/or biochemical characteristics of the antibodies and fragments described herein may be achieved by creating substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulkiness of the side chain. A "conservative amino acid substitution" may involve a substitution of a native amino acid residue with a normative residue that has little or no effect on the polarity or charge of the amino acid residue at that position. Furthermore, any native residue in the polypeptide may also be substituted with alanine, as has been previously described for alanine scanning mutagenesis.

Amino acid substitutions (whether conservative or non-conservative) of the subject antibodies can be implemented by those skilled in the art by applying routine techniques. Amino acid substitutions can be used to identify important residues of the antibody provided herein, or to increase or decrease the affinity of these antibodies for the IgE high affinity receptor (FcεRI) or for modifying the binding affinity of other antibodies described herein.

An antibody of the present invention may be prepared by any of a number of conventional techniques. For example, antibodies may be produced by recombinant expression systems, using any technique known in the art. See, for example, *Monoclonal Antibodies, Hybridomas: A New Dimension in Biological Analyses*, Kennet et al. (eds.) Plenum Press, New York (1980): and *Antibodies: A Laboratory Manual*, Harlow and Lane (eds.), Cold Spring Harbor Laboratory Press, Cold Spring Harbor, N.Y. (1988).

Antibodies of the present invention and binding fragments thereof can be produced in hybridoma cell lines or in cell lines other than hybridomas. Expression constructs encoding the antibodies can be used to transform a mammalian, insect or microbial host cell. Transformation can be performed using any known method for introducing polynucleotides into a host cell, including, for example packaging the polynucleotide in a virus or bacteriophage and transducing a host cell with the construct by transfection procedures known in the art, as exemplified by U.S. Pat. Nos. 4,399,216, 4,912,040, 4,740,461, and 4,959,455. The optimal transformation procedure used will depend upon which type of host cell is being transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

Recombinant expression constructs of the invention typically comprise a nucleic acid molecule encoding a polypeptide comprising one or more of the following: a heavy chain constant region; a heavy chain variable region; a light chain constant region; a light chain variable region; one or more CDRs of the light or heavy chain of the anti-canine IgE antibody. These nucleic acid sequences are inserted into an appropriate expression vector using standard ligation techniques. In one embodiment, the canine, equine, feline, or human antibody heavy or light chain constant region is appended to the C-terminus of the Canine IgE-specific heavy or light chain variable region and is ligated into an expression vector. The vector is typically selected to be functional in the particular host cell employed (i.e., the vector is compatible with the host cell machinery, permitting amplification and/or expression of the gene can occur). In some embodiments, vectors are used that employ protein-fragment complementation assays using protein reporters, such as dihydrofolate reductase.

Typically, expression vectors used in any of the host cells contain sequences for plasmid or virus maintenance and for cloning and expression of exogenous nucleotide sequences. Such sequences, collectively referred to as "flanking sequences" typically include one or more of the following operatively linked nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element.

Optionally, the vector may contain a "tag"-encoding sequence, that is, an oligonucleotide molecule located at the 5' or 3' end of the coding sequence, the oligonucleotide sequence encoding polyHis, or another "tag" for which commercially available antibodies exist, such as FLAG®™, HA (hemagglutinin from influenza virus), or myc. The tag is typically fused to the antibody protein upon expression, and can serve as a means for affinity purification of the antibody from the host cell. Affinity purification can be accomplished, for example, by column chromatography using antibodies against the tag as an affinity matrix. Optionally, the tag can subsequently be removed from the purified antibody polypeptide by various means such as using certain peptidases for cleavage.

Flanking sequences in the expression vector may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, column chromatography, or other methods known to the skilled artisan. The selection of suitable enzymes to accomplish this purpose will be readily apparent to those skilled in the art.

An origin of replication is typically a part of prokaryotic expression vectors, particularly those purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 is suitable for most gram-negative bacteria and various origins (e.g., SV40, polyoma, adenovirus, vesicular stomatitis virus (VSV), or papillomaviruses such as HPV or BPV) are useful for cloning vectors in mammalian cells. Generally, a mammalian origin of replication is not needed for mammalian expression vectors (for example, the SV40 origin is often used only because it contains the early promoter).

The expression and cloning vectors of the present invention will typically contain a promoter that is recognized by the host organism and operably linked to nucleic acid encoding the chimeric protein. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continuous gene product production; that is, there is little or no experimental control over gene expression. A large number of promoters, recognized by a variety of potential host cells, are well known. A suitable promoter is operably linked to the DNA encoding a chimeric protein by removing the promoter from the source DNA by restriction enzyme digestion or amplifying the promoter by polymerase chain reaction and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Particular promoters useful in the practice of the recombinant expression vectors of the invention include, but are not limited to: the SV40 early promoter region; the CMV promoter; the promoter contained in the 3' long terminal repeat of Rous sarcoma virus; the herpes thymidine kinase promoter; the regulatory sequences of the metallothionein; prokaryotic expression vectors such as the beta-lactamase promoter; or the tac promoter. Also available for use are the following animal transcriptional control regions, which exhibit tissue specificity and have been utilized in transgenic animals: the elastase I gene control region that is active in pancreatic acinar cells; the insulin gene control region that is active in pancreatic beta cells; the mouse mammary tumor virus control region that is active in testicular, breast, lymphoid and mast cells; the albumin gene control region that is active in; the alpha-feto-protein gene control region that is active in liver; the alpha 1-antitrypsin gene control region that is active in the liver; the beta-globin gene control region that is active in myeloid cells; the myelin basic protein gene control region that is active in oligodendrocyte cells in the brain; the myosin light chain-2 gene control region that is active in skeletal muscle; the gonadotropic releasing hormone gene control region that is active in the hypothalamus; and the immunoglobulin gene control region that is active in lymphoid.

An enhancer sequence may be inserted into the vector to increase the transcription in higher eukaryotes of a nucleic acid encoding a chimeric protein of the present invention. Enhancers are cis-acting elements of DNA, usually about 10-300 base pairs in length, that act on promoters to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). An enhancer sequence from a virus also can be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a nucleic acid molecule, it is typically placed at a site 5' to the promoter.

In expression vectors, a transcription termination sequence is typically located 3' of the end of a polypeptide-coding region and serves to terminate transcription. A transcription termination sequence used for expression in prokaryotic cells typically is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes used in expression vectors encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Examples of selectable markers include the kanamycin resistance gene, the ampicillin resistance gene and the tetracycline resistance gene. A bacterial neomycin resistance gene can also be used for selection in both prokaryotic and eukaryotic host cells.

Other selection genes can be used to amplify the gene that will be expressed. Amplification is a process whereby genes that cannot in single copy be expressed at high enough levels to permit survival and growth of cells under certain selection conditions are reiterated in tandem within the chromosomes of successive generations of recombinant cells. Examples of suitable amplifiable selectable markers for mammalian cells include dihydrofolate reductase (DHFR) and promoterless thymidine kinase. In the use of these markers mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively increased, thereby permitting survival of only those cells in which the selection gene has been amplified. Under these circumstances, DNA adjacent to the selection gene, such as DNA encoding an antibody of the invention, is co-amplified with the selection gene. As a result, increased quantities of chimeric protein are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, for example where glycosylation is desired in a eukaryotic host cell expression system, various presequences can be manipulated to improve glycosylation or yield. For example, the peptidase cleavage site of a particular signal peptide can be altered, or pro-sequences added, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated yet active form of the desired polypeptide, if the enzyme cuts at such area within the mature polypeptide.

Where a commercially available expression vector lacks some of the desired flanking sequences as described above, the vector can be modified by individually ligating these sequences into the vector. After the vector has been chosen and modified as desired, a nucleic acid molecule encoding a chimeric protein is inserted into the proper site of the vector.

The completed vector containing sequences encoding the inventive antibody or immunologically functional fragment thereof is inserted into a suitable host cell for amplification and/or polypeptide expression. The transformation of an expression vector for a chimeric protein into a selected host cell may be accomplished by well-known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan.

The transformed host cell, when cultured under appropriate conditions, synthesizes a chimeric protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, many immortalized cell lines available from the American Type Culture Collection (ATCC), such as Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, the best cell line for expressing a particular DNA construct may be selected by testing various cell lines to determine which ones have the highest levels of expression levels and produce antibodies with constitutive Canine IgE binding properties.

In addition to the foregoing, systems for the production of transgenic plants that produce transgenic antibodies, and from which the antibodies are collected, are known and can also be used to carry out the present invention. Examples of such plants, methods of making such plants, and methods of using such plants for the production and collection of antibodies are described in, for example, U.S. Pat. Nos. 8,071,333; 7,781,647; 7,736,648; 7,247,711; 6,852,319 6,841,659; 6,040,498; and 5,959,177.

An antibody of the present invention may be used as a therapeutic agent (e.g., to treat allergic disorders and/or diseases) and/or as a diagnostic agent (e.g., to monitor and/or evaluate anti-IgE treatment of a subject afflicted with an allergic disorder).

In certain embodiments, the invention provides compositions comprising an antibody of the present invention together with one or more of the following: a pharmaceutically acceptable diluent; a carrier; a solubilizer; an emulsifier; a preservative; and/or an adjuvant. Such compositions may contain an effective amount of the antibody. Thus, the use of the antibody provided herein in the preparation of a pharmaceutical composition or medicament is also included. Such compositions can be used in the treatment of a variety of allergic diseases and/or disorders.

Acceptable formulation components for pharmaceutical preparations are nontoxic to recipients at the dosages and concentrations employed. In addition to antibodies provided, compositions according to the invention may contain components for modifying, maintaining or preserving, for example, the pH, osmolarity, viscosity, clarity, color, isotonicity, odor, sterility, stability, rate of dissolution or release, adsorption or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants.

The primary vehicle or carrier in a pharmaceutical composition may be either aqueous or non-aqueous in nature. Suitable vehicles or carriers for such compositions include water for injection, physiological saline solution or artificial cerebrospinal fluid, possibly supplemented with other materials common in compositions for parenteral administration. Neutral buffered saline or saline mixed with serum albumin are further exemplary vehicles.

Compositions comprising antibodies of this invention may be prepared for storage by mixing the selected composition having the desired degree of purity with optional formulation agents in the form of a lyophilized cake or an aqueous solution. Further, the antibodies may be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

A pharmaceutical composition may involve an effective quantity of an antibody in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert materials, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions are in the form of sustained- or controlled-delivery formulations. Techniques for formulating a variety of other sustained- or controlled-delivery means, such as liposome carriers, bio-erodible microparticles or porous beads and depot injections can be. Sustained-release preparations may include semipermeable polymer matrices in the form of shaped articles, e.g. films, or microcapsules, polyesters, hydrogels, polylactides, copolymers of L-glutamic acid and gamma ethyl-L-glutamate, poly (2-hydroxyethyl-methacrylate), ethylene vinyl acetate or poly-D(−)-3-hydroxybutyric acid. Sustained release compositions may also include liposomes, which can be prepared by any of several methods known in the art.

The pharmaceutical composition to be used for in vivo administration typically is sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

The composition may be formulated for transdermal delivery, optionally with the inclusion of microneedles, microprojectiles, patches, electrodes, adhesives, backings, and/or packaging, or formulations for jet delivery, in accordance with known techniques. See, e.g., U.S. Pat. Nos. 8,043,250; 8,041,421; 8,036,738; 8,025,898; 8,017,146.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The present invention provides kits for producing multi-dose or single-dose administration units. For example, kits according to the invention may each contain both a first container having a dried protein and a second container having an aqueous diluent, including for example single and multi-chambered pre-filled syringes (e.g., liquid syringes, lyosyringes or needle-free syringes).

The pharmaceutical compositions of the invention can be delivered parenterally, typically by injection. Injections can be intraocular, intraperitoneal, intraportal, intramuscular, intravenous, intrathecal, intracerebral (intra-parenchymal), intracerebroventricular, intraarterial, intralesional, perilesional or subcutaneous. Eye drops can be used for intraocular administration. In some instances, injections may be localized to the vicinity of a particular bone or bones to which the treatment is targeted. For parenteral administration, the chimeric protein may be administered in a pyrogen-free, parenterally acceptable aqueous solution comprising the chimeric protein in a pharmaceutically acceptable vehicle. A particularly suitable vehicle for parenteral injection is sterile distilled water in which the chimeric proteins are formulated as a sterile, isotonic solution, properly preserved.

Pharmaceutical compositions comprising the subject antibody may be administered by bolus injection or continuously by infusion, by implantation device, sustained release systems or other means for accomplishing prolonged release. The pharmaceutical composition also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous release. The preparation may be formulated with agent, such as injectable microspheres, bio-erodible particles, polymeric compounds (such as polylactic acid; polyglycolic acid; or copoly (lactic/glycolic) acid (PLGA), beads or liposomes, that can provide controlled or sustained release of the product which may then be delivered via a depot injection. Formulation with hyaluronic acid has the effect of promoting sustained duration in the circulation.

The subject compositions comprising an antibody may be formulated for inhalation. In these embodiments, an antibody is formulated as a dry powder for inhalation, or antibody inhalation solutions may also be formulated with a propellant for aerosol delivery, such as by nebulization.

Certain pharmaceutical compositions of the invention can be delivered through the digestive tract, such as orally. The subject antibodies that are administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized. Additional agents can be included to facilitate absorption of the chimeric protein. For oral administration, modified amino acids may be used to confer resistance to digestive enzymes. Diluents, flavorings, low melting point waxes, vegetable oils, lubricants, suspending agents, tablet disintegrating agents, and binders may also be employed.

The subject compositions comprising antibodies also may be used ex vivo. In such instances, cells, tissues or organs that have been removed from the patient are exposed to or cultured with the antibody. The cultured cells may then be implanted back into the patient or a different patient or used for other purposes.

In certain embodiments, the invention also provides compositions comprising the subject antibody for diagnostic purposes. Such compositions comprise the subject antibody with one or more suitable compounds and/or agents that are known and/or are typically used and/or associated with formulations for diagnostic agents in the art. For example, in some embodiments, the subject diagnostic compositions comprise antibodies that may be used in vitro assays, such as in assays to determine the level of IgE high affinity receptor on monocytes and/or determine the level of free IgE high affinity receptor in a sample from a subject.

In certain embodiments, antibodies can be delivered by implanting certain cells that have been genetically engineered, using methods such as those described herein, to express and secrete the polypeptide. Such cells may be animal or human cells, and may be autologous, heterologous, or xenogenic, or may be immortalized. In order to decrease the chance of an immunological response, the cells may be encapsulated to avoid infiltration of surrounding tissues. Encapsulation materials are typically biocompatible, semi-permeable polymeric enclosures or membranes that allow the release of the protein product(s) but prevent the destruction of the cells by the patient's immune system or by other detrimental factors from the surrounding tissues.

A method of the present invention may be directed towards guiding, monitoring, and/or evaluating treatment in a subject in need thereof comprising the steps of administering an anti-IgE treatment to the subject and then measuring a level of IgE high affinity receptor in free form and/or on monocytes in a sample from the subject by contacting the sample with the antibody of this invention and detecting the level of IgE high affinity receptor in free form and/or on monocytes in the sample, wherein the level≥a threshold value identifies the subject as needing modifications of the administered IgE treatment and/or needing alternate treatment therapy.

The subject receiving treatment can be a canine, feline, equine, or human. In particular embodiments, the subject is a human. The subject evaluated by this method is afflicted with a disorder or condition in which reduction of free IgE levels would be beneficial and is currently receiving treatment for this condition (e.g., an anti-IgE treatment). Examples of such a disorder or conditions include, but are not limited to, allergic disorders comprising allergic inflammation and/or chronic inflammation. Examples of chronic inflammation include, but are not limited to, celiac disease, vasculitis, lupus, chronic obstructive pulmonary disease (COPD), irritable bowel disease (IBS), atherosclerosis, arthritis, systemic lupus erythematosus, multiple sclerosis, asthma, chronic peptic ulcer, sinusitis, tuberculosis, rheumatoid arthritis, periodontitis, ulcerative colitis, Crohn's disease, atopic dermatitis (eczema), rosacea, seborrheic dermatitis, and/or psoriasis. Examples of allergic inflammation include, but are not limited to, allergic rhinitis, atopic dermatitis, allergic asthma, allergic conjunctivitis, gastrointestinal inflammation, urticarial, oral-pharyngeal inflammation, latex allergy, and/or food allergy.

The anti-IgE treatment administered to the subject can be any anti-IgE treatment suitable for reducing free IgE levels. Exemplary anti-IgE treatment includes, but should not be limited to, anti-IgE antibodies and/or fragments thereof, e.g., omalizumab.

The sample obtained from the subject includes serum and/or plasma samples obtained, e.g., from venapuncture collected blood. Methods of measuring levels of IgE high affinity receptor on monocytes employ monocytes that are not separated from other blood cells and are selectively viewed by size and granularity properties standard in, e.g., flow cytometry analysis. Exemplary preparation methods of monocytes in whole blood include the collection of blood cells from venapuncture into EDTA anticoagulant which are washed with buffer, then incubated with the fluorescent labeled antibody specific for the high affinity receptor of IgE for one hour. After incubation the cells are washed and then nucleated cells are fixed while red blood cells are lysed in a fixation buffer. The cells are washed and then analyzed by, e.g., flow cytometry under gating conditions that separate granulocytes, monocytes and lymphocytes. Median fluorescence intensity of the monocyte gated cells is reported. Other detection methods may be used in addition to or instead of flow cytometry to measure levels of IgE high affinity receptor on monocytes. Measurements for free IgE high affinity receptors are carried out in an analogous manner using similar methods as just described.

The level of IgE high affinity receptor in free form and/or obtained on monocytes measured with the antibody of this invention can be above, the same, or below a threshold value.

Measured levels of IgE high affinity receptor in free form and/or obtained on monocytes that are the same or above of the suggested threshold value indicates that the administered anti-IgE treatment is not optimal and, thus, needs modification. Modification to the administered anti-IgE treatment includes, but should not be limited to, increasing the dosage of current anti-IgE treatment, increase frequency of dosing, and/or change the route of administration of the anit-IgE treatment. Modifications also includes alternating the current anti-IgE treatment, e.g., adding a second therapeutic agent to the current anti-IgE treatment or changing to a different treatment therapy employing different therapeutic agent(s). Thus, in some embodiments, the method further comprises the step of administering a modified IgE treatment and/or administering an alternate treatment therapy to the subject Measured levels of IgE high affinity receptor in free form and/or obtained on monocytes that are lower than the suggested threshold value indicates that the administered anti-IgE treatment is optimal and, thus, no modification is necessary.

According to some embodiments provided is a method of using an antibody of the present invention for detecting and/or quantifying IgE high affinity receptor in a sample. The sample can be any one of the samples described above. A variety of protocols for detecting the presence of and/or measuring the amount of specific target molecular (e.g., high affinity receptor) in a sample, using the antibodies of this invention are known in the art. Examples of such protocols include, but are not limited to, enzyme immunoassays (EIA), agglutination assays, immunoblots (Western blot; dot/slot blot, etc.), radioimmunoassays (RIA), immunodiffusion assays, chemiluminescence assays, antibody library screens, expression arrays, enzyme-linked immunosorbent assays (ELISA), radioimmunoassays (RIA), immunoprecipitation, Western blotting, competitive binding assays, immunofluorescence, immunohistochemical staining precipitation/flocculation assays and fluorescence-activated cell sorting (FACS), "sandwich" immunoassays, immunoradiometric assays, gel diffusion precipitation reactions, in situ immunoassays (e.g., using colloidal gold, enzyme or radio-isotope labels, for example), precipitation reactions, agglutination assays (e.g., gel agglutination assays, hemagglutination assays, etc.), complement fixation assays, protein A assays, flow cytometry, and immunoelectrophoresis assays, etc. One example of an immunoassay is described in U.S.

Pat. Nos. 5,599,677 and 5,672,480, the disclosure of each of which is herein incorporated by reference. These and other assays are described, among other places, in Hampton et al. (*Serological Methods, a Laboratory Manual*, APS Press, St Paul, Minn (1990)) and Maddox et al. (*J. Exp. Med.* 158: 1211-1216 (1993)).

For example, numerous protocols for competitive binding or immunoradiometric assays using either polyclonal or monoclonal antibodies with established specificity are well known in the art. Such immunoassays typically involve the measurement of complex formation between an antigen and its specific antibody (e.g., antigen/antibody complex formation). A two-site, monoclonal-based immunoassay utilizing monoclonal antibodies reactive to two non-interfering epitopes on the polypeptides or peptides of this invention can be used as well as a competitive binding assay.

In some embodiments, antibodies can be conjugated to a solid support (e.g., beads, plates, slides or wells formed from materials such as latex or polystyrene) in accordance with known techniques. Antibodies can likewise be conjugated to detectable groups such as radiolabels (e.g., $^{35}S$, $^{125}I$, $^{131}I$), enzyme labels (e.g., horseradish peroxidase, alkaline phosphatase), and fluorescence labels (e.g., fluorescein) in accordance with known techniques. Determination of the formation of an antibody/antigen complex in the methods of this invention can be by detection of, for example, precipitation, agglutination, flocculation, radioactivity, color development or change, fluorescence, luminescence, etc., as is well known in the art. The phrase "detection molecule" is used herein in its broadest sense to include any molecule that can bind with sufficient specificity to a biomarker to allow for detection of the particular biomarker. To allow for detection can mean to determine the presence or absence of the particular biomarker member and, in some embodiments, can mean to determine the amount of the particular biomarker. Detection molecules can include, but are not limited to antibodies, antibody fragments, and nucleic acid sequences.

Upon review of the present disclosure, those skilled in the art will be familiar with numerous specific immunoassay formats and variations thereof that can be useful for carrying out the methods of the presently disclosed subject matter.

Subjects to be treated by a method and/or composition of the present invention include any afflicted with a disorder or condition in which reduction of free IgE levels would be beneficial. The subject receiving treatment can be a canine, feline, equine, or human. In particular embodiments, the subject is a human. Examples of disorders or conditions in which reduction of free IgE levels is desirable are the same allergic disorders mentioned above.

A pharmaceutical composition of the present invention may be administered for a prophylactic and/or therapeutic treatment. An "effective amount" refers generally to an amount that is a sufficient, but non-toxic, amount of the active ingredient (e.g., anti-IgE biologic agent, chimeric protein) to achieve the desired effect, which is a reduction or elimination in the severity and/or frequency of symptoms and/or improvement or remediation of damage (e.g., a reduction of flares, delays, relapses, and/or recurrences of lesions in a subject with atopic dermatitis). A "therapeutically effective amount" refers to an amount that is sufficient to remedy a disease state or symptoms, or otherwise prevent, hinder, retard or reverse the progression of a disease or any other undesirable symptom. A "prophylactically effective amount" refers to an amount that is effective to prevent, hinder or retard the onset of a disease state or symptom.

In general, toxicity and therapeutic efficacy of the antibody or fragment can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred.

The data obtained from cell culture and/or animal studies can be used in formulating a range of dosages for subjects for treatment. The dosage of the active ingredient typically lines within a range of circulating concentrations that include the $ED_{50}$ with little or no toxicity. The dosage can vary within this range depending upon the dosage form employed and the route of administration utilized.

The effective amount of a pharmaceutical composition comprising antibodies to be employed therapeutically or prophylactically will depend, for example, upon the therapeutic context and objectives. One skilled in the art will appreciate that the appropriate dosage levels for treatment, according to certain embodiments, will thus vary depending, in part, upon the molecule delivered, the indication for which the chimeric protein is being used, the route of administration, and the size (body weight, body surface or organ size) and/or condition (the age and general health) of the subject. Clinicians may titer the dosage and modify the route of administration to obtain the optimal therapeutic effect. Typical dosages range from about 1.0 µg/Kg to about 500 mg/Kg body weight (e.g., from about 1.0 µg/Kg to about 100 µg/Kg, or from about 500 µg/Kg to about 1 mg/Kg, or from about 5 mg/Kg to about 100 mg/Kg subject body weight), or more.

The dosing frequency will depend upon the pharmacokinetic parameters of antibody in the formulation. For example, a clinician will administer the composition until a dosage is reached that achieves the desired effect. The composition may therefore be administered as a single dose or as two or more doses (which may or may not contain the same amount of the desired molecule) over time, or as a continuous infusion via an implantation device or catheter. Treatment may be continuous over time or intermittent. Further refinement of the appropriate dosage is routinely made by those of ordinary skill in the art and is within the ambit of tasks routinely performed by them. Appropriate dosages may be ascertained through use of appropriate dose-response data.

To treat a disorder characterized by abnormal or excess expression of IgE, a composition comprising the subject antibody may be administered to the patient in an amount and for a time sufficient to induce a sustained improvement in at least one indicator that reflects the severity of the disorder. An improvement is considered "sustained" if the patient exhibits the improvement on at least two occasions separated by at least one to seven days, or in some instances one to six weeks. The appropriate interval will depend to some extent on what disease condition is being treated; it is within the purview of those skilled in the art to determine the appropriate interval for determining whether the improvement is sustained. The degree of improvement is determined based on signs or symptoms, and may also employ questionnaires that are administered to the patient, such as quality-of-life questionnaires.

According to some embodiments of the present invention a kit is provided. A kit may include an antibody and/or a pharmaceutical composition of the present invention. Some kits include such antibody and/or composition in a container (e.g., vial or ampule), and may also include instructions for use of same antibody and/or composition in the various methods disclosed above. The antibody or composition can be in various forms, including, for instance, as part of a solution or as a solid (e.g., lyophilized powder). The instructions may include a description of how to prepare (e.g., dissolve or resuspend) the antibody in an appropriate fluid and/or how to administer the antibody for the treatment of the allergic disease and/or disorder.

The kits may also include various other components, such as buffers, salts, complexing metal ions and other agents described above in the section on pharmaceutical compositions. These components may be included with the antibody or may be in separate containers. The kits may also include other therapeutic agents for administration with the antibody.

The following examples are provided solely to illustrate certain aspects of the antibodies, fragments and compositions that are provided herein and thus should not be construed to limit the scope of the claimed invention.

EXAMPLES

Example 1: Antibody Specific Epitope of High Affinity Receptor for IgE with Prognostic and Therapeutic Applications An epitope of the alpha chain of the high affinity receptor for IgE (FcεRIα) that is distant from the sites bound by IgE has been identified for generation of antibodies that aid prognosis of anti-IgE therapy and target biological therapy to IgE-dependent inflammatory cells. The IgE binding site on FcεRIα involves two distinct and spatially complex locations that can interact with and compromise the affinity of antibodies developed against FcεRIα when IgE is bound. A clinical trial with allergic dogs manifesting atopic dermatitis signs treated with an anti-IgE biological chimera of single chain variable fragment antibody specific for IgE linked to FcεRIα, demonstrated that duration of protection from return of clinical signs was correlated with the level of FcεRIα measured on blood monocytes by flow cytometry using the monoclonal antibody specific for the novel epitope on FcεRIα. The pre-treatment measurement of FcεRIα on circulating monocytes correlated inversely with duration of protection better than the current gold standard pre-treatment measurement of total circulating IgE (Table 1). This level of correlation aids the prognosis of anti-IgE therapy of allergic diseases permitting accurate patient selection for anti-IgE therapy. It also facilitates personalized dosage with anti-IgE biologicals.

The ability of the monoclonal antibody specific for the unique epitope on FcεRIα to bind FcεRIα while the receptor is binding IgE permits the development of a new approach to biological therapy for allergic diseases. FcεRIα expression on dendritic cells, basophils and mast cells is essential for the inflammatory response seen in allergic diseases. These cells also express a surface receptor for IgG called IgGγRIIb that sends a strong inhibitory signal when bound. The linkage of an anti-FcεRIα antibody fragment to an anti-IgGγRIIb antibody fragment will inhibit FcεRIα-bearing inflammatory cells from contributing to allergic inflammation.

Materials and Methods

The amino acid sequence CNGNNFFEVSSTKWFHNGS (SEQ ID NO:1) that represents the 26-44 amino acids from the amino terminal end of human FcεRIα chain and the canine and equine homologous sequences of FcεRIα, represented as the sequence CTGNNSLEVDSAVWLHNNT (SEQ ID NO:2) for the dog and the sequence CNKNKPLKGNSTEWTYNNT (SEQ ID NO:3) for the horse were used to generate sequence-specific rabbit polyclonal antibodies and sequence-specific mouse monoclonal antibodies. These antibodies bind native and recombinant produced FcεRIα chain from dog, horse and human attached to plastic microtiter plates and detected by ELISA. The binding is inhibited completely by each specific 19 mer amino acid peptide respectively for canine, equine and human FcεRIα.

A single chain variable fragment (scFv) specific for canine FcεRIα sequence CTGNNSLEVDSAVWLHNNT (SEQ ID NO:2) was generated by transfection of human embryonic kidney cell line HEK 293 with a plasmid containing the DNA sequences of the variable light chain and variable heavy chain of the mouse monoclonal antibody specific for canine FcεRIα sequence CTGNNSLEVDSAVWLHNNT (SEQ ID NO:2). The nucleotide sequence of anti-canine FcεRIα scFv construct is shown in FIG. 1 and the amino acid sequence of this scFv that specifically binds canine FcεRIα is shown in FIG. 2. This sequence includes an amino acid bridge of $(G_4S)_3$. The complementarity-determining regions (CDR) sequences for this anti-FcεRIα chain antibody are as follows:

```
Variable Heavy region:
CDR1-
                                    (SEQ ID NO: 7)
SGFWN,

CDR2-
                                    (SEQ ID NO: 8)
YISYSGSTYYNPSLKS,

CDR3-
                                    (SEQ ID NO: 9)
GDMRYNAWFAY

Variable Light region:
CDR1-
                                    (SEQ ID NO: 4)
RSSQSLVHSNGNTYLH,

CDR2-
                                    (SEQ ID NO: 5)
KVSNRFS,

CDR3-
                                    (SEQ ID NO: 6)
SQSTHAPPT
```

FcεRIα complexed with IgE is less detectable than uncomplexed FcεRIα. The high inverse correlation between circulating monocyte expression of FcεRIα and duration of protection from return of allergic flare episodes during treatment with anti-IgE biologicals is unexpected. Current evaluation of efficacy for anti-IgE biological treatments in humans rely on measurement of levels of circulating IgE; however, even though reduction in serum IgE is consistently associated with treatment there is less evidence for correlation between pre-treatment levels and clinical outcomes of anti-IgE treatment.

Applications

As anti-IgE biological treatment for allergic diseases of humans over the past 15 years has increased and similar treatments for allergic dogs are being introduced, the ability to select individuals with greatest potential for positive outcomes has a high commercial value. In addition, effective dosage discovered for individuals is greatly facilitated by measurement of pre-treatment levels of FcεRIα expression on circulating monocytes just as is currently practiced for human dosage of anti-IgE omalizumab by measurement of circulating IgE. However, the measurement of expression of FcεRIα is a more accurate predictor of treatment outcome, as seen in allergic dogs (Table 1), and thereby appropriate dosage.

Table 1 shows measurements of FcεRIα expression as MFI by flow cytometry using fluorescence-labelled monoclonal antibody specific for the canine FcεRIα chain peptide sequence CTGNNSLEVDSAVWLHNNT (SEQ ID NO:2). Dogs were treated with three biweekly injections of anti-IgE chimera while on anti-inflammatory medication to protect against allergic flare return after stopping anti-inflammatory medication (corticosteroids).

Supporting Data of Applications

The high prognostic value of this FcεRIα-specific antibody for successful response to anti-IgE therapy is demonstrated in Table 1. The functional ability to measure FcεRIα levels of expression on cells is shown in FIG. 3, where a canine mast cell line with high binding ability for canine IgE to its surface FcεRIα demonstrated no inhibition of binding by the antibody specific for FcεRIα epitope CTGNNSLEVDSAVWLHNNT (SEQ ID NO:2) in the presence of pre-bound IgE. Specifically, mouse monoclonal anti-FcεRIα labeled with FITC or mouse IgG2b isotype control labeled with FITC was incubated with the canine mast cell line HMRC cells that were pre-incubated with canine IgE or not. In addition, mAb anti FcεRIα was pre-incubated with the FcεRIα peptide sequence CTGNNSLEVDSAVWLHNNT (SEQ ID NO:2) to demonstrate specificity of binding. The median fluorescence intensity (MIF) for each of the conditions is as follows:
  a. mouse isotype control—1720.03
  b. mouse mAb anti FcεRIα+peptide CTGNNSLEVDSAVWLHNNT (SEQ ID NO:2)—1702.80
  c. mouse mAb anti FcεRIα with no IgE pre-incubation of mast cells—3340.90
  d. mouse mAb anti FcεRIα with IgE pre-incubated mast cells—3323.20

Example 2: Cellular Expression of the High Affinity Receptor for IgE (FcεRI) in Dogs Treated with a Therapeutic Chimera of Anti-IgE Monoclonal Antibody Single Chain Fragment (scFv) Linked to FcεRI Alpha Chain Biomarkers that correlate with high fidelity with the risk of atopic dermatitis would be of major importance as diagnostic and prognostic tools. Canine atopic dermatitis closely mimics human atopic dermatitis in pathogenesis and clinical presentation. Serum immunoglobulin E (IgE), measured as allergen-specific and as total circulating levels, have limited stand-alone value, but they do support diagnosis based on clinical signs and intradermal skin testing with suspect allergens. The success of anti-IgE monoclonal antibodies in treatment of human allergic asthma has encouraged the development of anti-IgE biologicals for treatment of atopic dermatitis in dogs. In both humans and dogs reduction of FcεRI expression on peripheral blood cells (PBC) has been used as a biomarker for drug effect. This is measured indirectly in humans by binding of labelled IgE by cells after removal of autologous IgE by lactic acid stripping. Unfortunately lactic acid stripping is incomplete in humans and does not remove autologous IgE from canine PBC. To circumvent this obstacle to evaluation of anti-IgE therapy in atopic dermatitis, we developed a mouse monoclonal antibody with high affinity for an epitope on canine FcεRI that permits recognition of cell surface FcεRI in the presence or absence of IgE. In addition to monitoring the reduction of plasma IgE, PBC expression of the FcεRI was monitored in dogs after injection of a chimera of anti-IgE single chain variable fragment (scFv 5.91) linked to FcεRI alpha chain by flow cytometry using the newly developed monoclonal antibody. It was concluded that reduction in cellular expression of FcεRI was more closely associated with the long-term response to anti-IgE scFv 5.91×FcεRI alpha chain treatment than total plasma IgE reduction (Table 1)

Example 3: Cellular Expression of the High Affinity Receptor for IgE (FcεRI) in Dogs Treated with a Therapeutic Chimera of Anti-IgE Monoclonal Antibody Single Chain Fragment (scFv) Linked to FcεRI Alpha Chain-Identification of Potential Biomarkers for Clinical Response to Treatment From observed broad ranges of clinical responses to anti-IgE therapy it is clear that the identification of a biomarker that correlates with clinical outcome would be valuable for selective treatment and for dose discovery. During a clinical trial dogs were monitored by flow cytometry of peripheral blood cell expression of FcεRI alpha chain (FIG. 3). Measurement of plasma IgE is used during treatment of humans with anti-IgE omalizumab. The involvement of FcεRI alpha chain in many aspects of IgE function indicated including it in this search for a useful biomarker.

Figure 4:
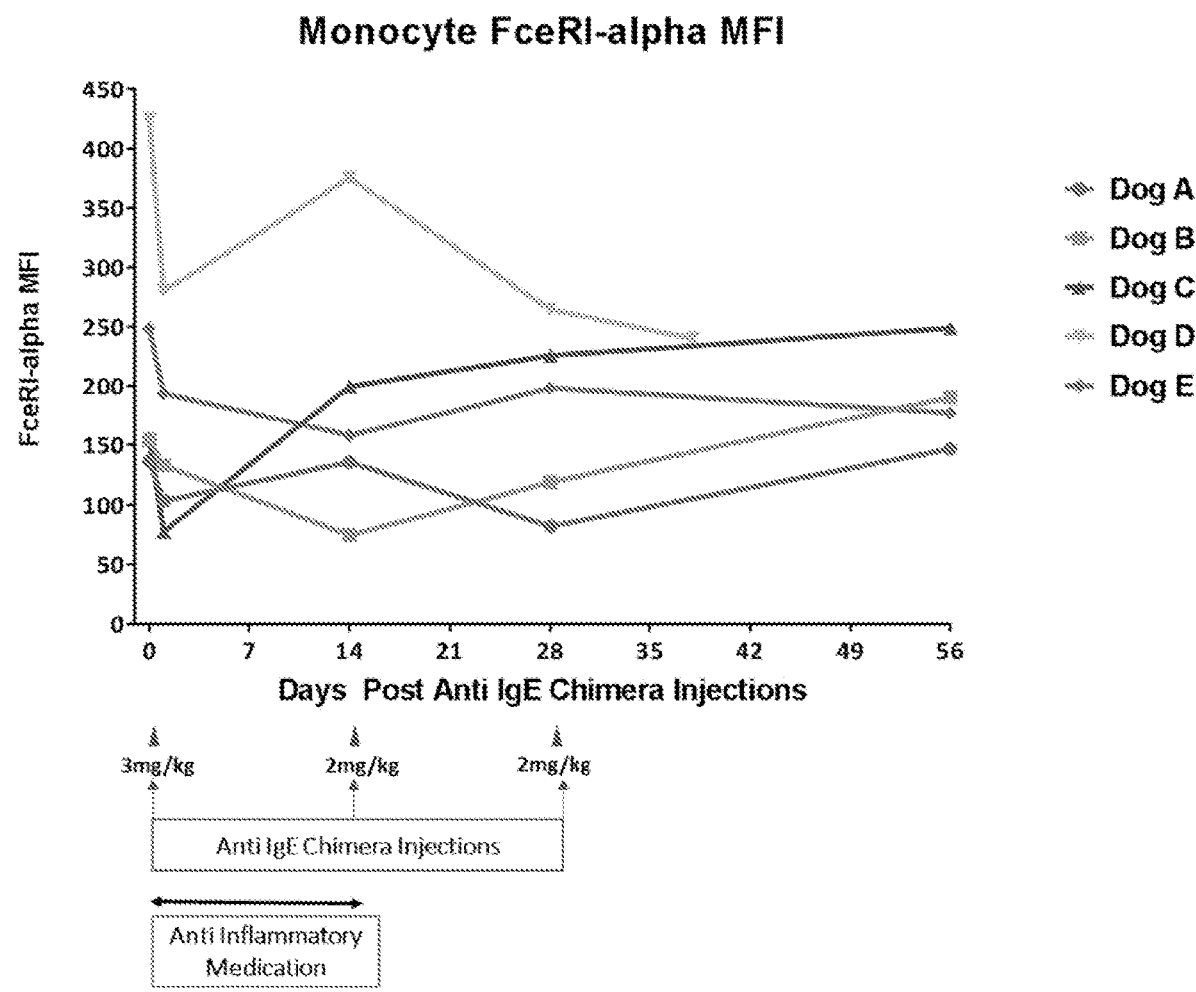
FIG. 4. Measurement of median fluorescence intensity (MFI) of surface expression of FcεRI alpha chain on peripheral blood cells (PBC) monocyte-gated by forward scatter and side scatter.

FIG. 4 shows an antibody specific for canine FcεRI alpha chain that was labeled with APC for direct measurement of MFI on un-fixed whole blood samples. Staining with anti-FcεRI alpha chain Ab was at 5 µg/ml for 60 minutes at 4° C. As with plasma IgE levels, there was a wide range of pre-injection expression levels, from 136.71 to 424.85 MFI. All dogs showed reduction in expression 24 hours after the first injection of anti-IgE chimera.

TABLE 1

Biomarkers predictive of response to anti-IgE therapy

| Dog | Monocyte FcεRI-alpha expression Median Fluorescence Intensity (MFI) | Free IgE in plasma detection by FcεRI-alpha ELISA (ug/ml) | Duration of protection from flare after medication stopped in days |
|---|---|---|---|
| A | 136.71 | 11.31 | 216 |
| B | 154.38 | 0.86 | 124 |
| C | 155.87 | 54.26 | 56 |
| D | 424.85 | 31.34 | 21 |
| E | 248.85 | 16.27 | 48 |
|   | Spearman's Correlation Coefficient = −1 $p < 0.0001$ | Spearman's Correlation Coefficient = −0.6 $p = 0.2848$ | |

The foregoing is illustrative of the present invention, and is not to be construed as limiting thereof. The invention is defined by the following claims, with equivalents of the claims to be included therein.

That which is claimed is:

1. An antibody that binds to IgE high affinity receptor (FcεRIα) at an epitope within the amino acid sequence CNGNNFFEVSSTKWFHNGS (SEQ ID NO:1) of human FcεRIα or at an epitope within the corresponding amino acid sequence of a different mammalian species, wherein the antibody is a scFv that comprises:

(i) a light chain (LC) variable region having at complementarity determining regions (CDRs) the amino acid sequences of:

```
                              (LC CDR1; SEQ ID NO: 4)
RSSQSLVHSNGNTYLH;

(LC CDR2; SEQ ID NO: 5)
KVSNRFS;
and (LC CDR3; SEQ ID NO: 6)
SQSTHAPPT;
and
```

(ii) a heavy chain (HC) variable region having at complementarity determining regions (CDRs) the amino acid sequences of:

```
                              (HC CDR1; SEQ ID NO: 7)
SGFWN;

(HC CDR2; SEQ ID NO: 8)
YISYSGSTYYNPSLKS;
and (HC CDR3; SEQ ID NO: 9)
GDMRYNAWFAY,
and
``` wherein the antibody binds to canine FcεRIα at an epitope within the amino acid sequence CTGNNSLEVDSAVWLHNNT (SEQ ID NO:2).

2. The antibody of claim 1 that binds to equine FcεRIα at an epitope within the amino acid sequence CNKNKPLKGNSTEWTYNNT (SEQ ID NO:3).

3. The antibody of claim 1, wherein the scFv comprises: the amino acid sequence of SEQ ID NO:14; a linker sequence; and the amino acid sequence of SEQ ID NO: 10.

4. The antibody of claim 3, wherein the linker sequence comprises amino acid sequence: GGGGGGGGSGGGGS (SEQ ID NO:11).

5. The antibody of claim 1, wherein the scFv comprises the amino acid sequence:

```
                                       (SEQ ID NO: 12)
METDTLLLWVLLLWVPGSTGDEVQLQESGPSLVKPSQTLSLTCSVTGDS

ITSGFWNWIRKFPGNKLEYMGYISYSGSTYYNPSLKSRISITRDTSKNQ

YYLQLNSVTTADTATYYCARGDMRYNAWFAYWGQGTLVTVSAGGGGSGG

GGSGGGGSDVVMTQTPLSLPVSLGDQASISCRSSQSLVHSNGNTYLHWY

LQKPGQSPKLLIYKVSNRFSGVPDRFSGSGSGTDFTLKISRVEAEDLGV

YFCSQSTHAPPTFGGGTKLEIK.
```

6. The antibody of claim 1, wherein the scFv is humanized, caninized, felinized, or equinized.

7. The antibody of claim 1, further comprising a water soluble polyalkylene oxide group coupled thereto.

8. The antibody of claim 7, wherein said water soluble polyalkylene oxide group comprises polyethylene glycol.

9. The antibody of claim 1, wherein the single chain variable fragment (scFv) forms an antigen-binding monomer.

10. A composition comprising the antibody of claim 1 in a pharmaceutically acceptable carrier.

11. A recombinant nucleic acid molecule encoding the antibody of claim 1.

12. A composition comprising the recombinant nucleic acid molecule of claim 11 in a pharmaceutically acceptable carrier.

13. A host cell comprising the recombinant nucleic acid molecule of claim 11.

14. The host cell of claim 13, wherein said cell is a bacterial cell, a yeast cell, a mammalian cell in culture, or a plant cell.

* * * * *

UNITED STATES PATENT AND TRADEMARK OFFICE
CERTIFICATE OF CORRECTION

PATENT NO. : 12,060,437 B2  
APPLICATION NO. : 16/982765  
DATED : August 13, 2024  
INVENTOR(S) : Hammerberg et al.

Page 1 of 1

It is certified that error appears in the above-identified patent and that said Letters Patent is hereby corrected as shown below:

In the Claims

Column 40, Line 6, Claim 4: Please correct "GGGGGGGGSGGGGS" to read --GGGGSGGGGSGGGGS--

Signed and Sealed this  
Twenty-seventh Day of May, 2025

Coke Morgan Stewart  
*Acting Director of the United States Patent and Trademark Office*

SEQUENCE LISTING

<160> NUMBER OF SEQ ID NOS: 14

<210> SEQ ID NO 1
<211> LENGTH: 19
<212> TYPE: PRT
<213> ORGANISM: Homo sapiens

<400> SEQUENCE: 1

Cys Asn Gly Asn Asn Phe Phe Glu Val Ser Ser Thr Lys Trp Phe His
1               5                   10                  15

Asn Gly Ser

<210> SEQ ID NO 2
<211> LENGTH: 19
<212> TYPE: PRT
<213> ORGANISM: Canine

<400> SEQUENCE: 2

Cys Thr Gly Asn Asn Ser Leu Glu Val Asp Ser Ala Val Trp Leu His
1               5                   10                  15

Asn Asn Thr

<210> SEQ ID NO 3
<211> LENGTH: 19
<212> TYPE: PRT
<213> ORGANISM: Equine

<400> SEQUENCE: 3

Cys Asn Lys Asn Lys Pro Leu Lys Gly Asn Ser Thr Glu Trp Thr Tyr
1               5                   10                  15

Asn Asn Thr

<210> SEQ ID NO 4
<211> LENGTH: 16
<212> TYPE: PRT
<213> ORGANISM: Artificial Sequence
<220> FEATURE:
<223> OTHER INFORMATION: CDR1 of antibody binding to IgE high affinity
      receptor.

<400> SEQUENCE: 4

Arg Ser Ser Gln Ser Leu Val His Ser Asn Gly Asn Thr Tyr Leu His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: LC CDR2 of antibody binding to IgE high
      affinity receptor.

<400> SEQUENCE: 5

Lys Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: LC CDR3 of antibody binding to IgE high
      affinity receptor

<400> SEQUENCE: 6

```
Ser Gln Ser Thr His Ala Pro Pro Thr
1               5

<210> SEQ ID NO 7
<211> LENGTH: 5
<212> TYPE: PRT
<213> ORGANISM: Artificial Sequence
<220> FEATURE:
<223> OTHER INFORMATION: HC CDR1 of antibody bidning to IgE high
      affinity receptor

<400> SEQUENCE: 7

Ser Gly Phe Trp Asn
1               5

<210> SEQ ID NO 8
<211> LENGTH: 16
<212> TYPE: PRT
<213> ORGANISM: Artificial Sequence
<220> FEATURE:
<223> OTHER INFORMATION: HC CDR2 of antibody binding to IgE high
      affinity receptor

<400> SEQUENCE: 8

Tyr Ile Ser Tyr Ser Gly Ser Thr Tyr Tyr Asn Pro Ser Leu Lys Ser
1               5                   10                  15

<210> SEQ ID NO 9
<211> LENGTH: 11
<212> TYPE: PRT
<213> ORGANISM: Artificial Sequence
<220> FEATURE:
<223> OTHER INFORMATION: HC CDR3 of antibody binding to IgE high
      affinity receptor

<400> SEQUENCE: 9

Gly Asp Met Arg Tyr Asn Ala Trp Phe Ala Tyr
1               5                   10

<210> SEQ ID NO 10
<211> LENGTH: 112
<212> TYPE: PRT
<213> ORGANISM: Artificial Sequence
<220> FEATURE:
<223> OTHER INFORMATION: a portion of exemplary scFv

<400> SEQUENCE: 10

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ala Pro Pro Thr Phe Gly Gly Gly Thr Lys Leu Glu Ile Lys
            100                 105                 110

<210> SEQ ID NO 11
```

```
<211> LENGTH: 15
<212> TYPE: PRT
<213> ORGANISM: Artificial Sequence
<220> FEATURE:
<223> OTHER INFORMATION: linker sequence

<400> SEQUENCE: 11

Gly Gly Gly Gly Ser Gly Gly Gly Gly Ser Gly Gly Gly Gly Ser
1               5                   10                  15

<210> SEQ ID NO 12
<211> LENGTH: 267
<212> TYPE: PRT
<213> ORGANISM: Artificial Sequence
<220> FEATURE:
<223> OTHER INFORMATION: single chain variable fragment (scFv) of
      antibody bindting to IgE high affinity receptor.

<400> SEQUENCE: 12

Met Glu Thr Asp Thr Leu Leu Leu Trp Val Leu Leu Trp Val Pro
1               5                   10                  15

Gly Ser Thr Gly Asp Glu Val Gln Leu Gln Glu Ser Gly Pro Ser Leu
                20                  25                  30

Val Lys Pro Ser Gln Thr Leu Ser Leu Thr Cys Ser Val Thr Gly Asp
        35                  40                  45

Ser Ile Thr Ser Gly Phe Trp Asn Trp Ile Arg Lys Phe Pro Gly Asn
    50                  55                  60

Lys Leu Glu Tyr Met Gly Tyr Ile Ser Tyr Ser Gly Ser Thr Tyr Tyr
65              70                  75                  80

Asn Pro Ser Leu Lys Ser Arg Ile Ser Ile Thr Arg Asp Thr Ser Lys
                85                  90                  95

Asn Gln Tyr Tyr Leu Gln Leu Asn Ser Val Thr Thr Ala Asp Thr Ala
            100                 105                 110

Thr Tyr Tyr Cys Ala Arg Gly Asp Met Arg Tyr Asn Ala Trp Phe Ala
        115                 120                 125

Tyr Trp Gly Gln Gly Thr Leu Val Thr Val Ser Ala Gly Gly Gly Gly
    130                 135                 140

Ser Gly Gly Gly Gly Ser Gly Gly Gly Gly Ser Asp Val Val Met Thr
145                 150                 155                 160

Gln Thr Pro Leu Ser Leu Pro Val Ser Leu Gly Asp Gln Ala Ser Ile
                165                 170                 175

Ser Cys Arg Ser Ser Gln Ser Leu Val His Ser Asn Gly Asn Thr Tyr
            180                 185                 190

Leu His Trp Tyr Leu Gln Lys Pro Gly Gln Ser Pro Lys Leu Leu Ile
        195                 200                 205

Tyr Lys Val Ser Asn Arg Phe Ser Gly Val Pro Asp Arg Phe Ser Gly
    210                 215                 220

Ser Gly Ser Gly Thr Asp Phe Thr Leu Lys Ile Ser Arg Val Glu Ala
225                 230                 235                 240

Glu Asp Leu Gly Val Tyr Phe Cys Ser Gln Ser Thr His Ala Pro Pro
                245                 250                 255

Thr Phe Gly Gly Gly Thr Lys Leu Glu Ile Lys
            260                 265

<210> SEQ ID NO 13
<211> LENGTH: 823
<212> TYPE: DNA
<213> ORGANISM: Artificial Sequence
<220> FEATURE:
```

<223> OTHER INFORMATION: nucleotide sequence of scfV anti-canine
      construct

<400> SEQUENCE: 13
ggcgcgccac catggagaca gacacactcc tgctatgggt actgctgctc tgggttccag    60
gttccactgg tgacgaggtg cagcttcagg agtcaggacc tagcctcgtg aaaccttctc   120
agactctgtc cctcacctgt tctgtcactg gcgactccat caccagtggt ttctggaact   180
ggatccggaa attcccaggg aataaacttg agtacatggg gtacataagc tacagtggta   240
gcacttacta caatccatct ctcaaaagtc gaatctccat cactcgagac acatccaaga   300
accagtacta cctacagttg aattctgtga ctactgcgga cacagccaca tattactgtg   360
caagagggga tatgaggtac aacgcctggt ttgcttactg gggccaaggg actctggtca   420
ctgtctctgc aggaggtgga ggttctggag gtggaggttc aggaggtgga ggtagtgatg   480
ttgtgatgac ccaaactcca ctctccctgc ctgtcagtct tggagatcaa gcctccatct   540
cttgcagatc tagtcagagc cttgtacaca gtaatggaaa cacctattta cattggtacc   600
tgcagaagcc aggccagtct ccaaagctcc tgatctacaa agtttccaac cgattttctg   660
gggtcccaga caggttcagt ggcagtggat cagggacaga tttcacactc aagatcagca   720
gagtggaggc tgaggatctg ggagtttatt tctgctctca aagtacacat gctcctccca   780
cgttcggagg ggggaccaag ctggaaataa aataagcggc cgc                     823

<210> SEQ ID NO 14
<211> LENGTH: 140
<212> TYPE: PRT
<213> ORGANISM: Artificial Sequence
<220> FEATURE:
<223> OTHER INFORMATION: a portion of exemplary scFv

<400> SEQUENCE: 14

Met Glu Thr Asp Thr Leu Leu Trp Val Leu Leu Trp Val Pro
1               5                   10                  15

Gly Ser Thr Gly Asp Glu Val Gln Leu Gln Glu Ser Gly Pro Ser Leu
            20                  25                  30

Val Lys Pro Ser Gln Thr Leu Ser Leu Thr Cys Ser Val Thr Gly Asp
        35                  40                  45

Ser Ile Thr Ser Gly Phe Trp Asn Trp Ile Arg Lys Phe Pro Gly Asn
    50                  55                  60

Lys Leu Glu Tyr Met Gly Tyr Ile Ser Tyr Ser Gly Ser Thr Tyr Tyr
65                  70                  75                  80

Asn Pro Ser Leu Lys Ser Arg Ile Ser Ile Thr Arg Asp Thr Ser Lys
                85                  90                  95

Asn Gln Tyr Tyr Leu Gln Leu Asn Ser Val Thr Thr Ala Asp Thr Ala
            100                 105                 110

Thr Tyr Tyr Cys Ala Arg Gly Asp Met Arg Tyr Asn Ala Trp Phe Ala
        115                 120                 125

Tyr Trp Gly Gln Gly Thr Leu Val Thr Val Ser Ala
    130                 135                 140